United States Patent
Khoshnejad et al.

(10) Patent No.: US 11,389,577 B2
(45) Date of Patent: Jul. 19, 2022

(54) MULTIPURPOSE WEARABLE ENDOVASCULAR APPARATUS

(71) Applicant: Naamira Biomedicals LLC, Baytown, TX (US)

(72) Inventors: Mani Khoshnejad, Houston, TX (US); Athena Brelis Osbourne, Nashua, NH (US); Paul Michael Cecelya, Hudson, MA (US); Elizabeth Nelson, Wellesley, MA (US); Timothy Looney, Tyngsborough, MA (US)

(73) Assignee: Naamira Biomedicals LLC

( * ) Notice: Subject to any disclaimer, the term of this patent is extended or adjusted under 35 U.S.C. 154(b) by 0 days.

(21) Appl. No.: 17/342,279

(22) Filed: Jun. 8, 2021

(65) Prior Publication Data

US 2021/0290909 A1    Sep. 23, 2021

Related U.S. Application Data

(63) Continuation-in-part of application No. PCT/US2019/065954, filed on Dec. 12, 2019.

(Continued)

(51) Int. Cl.
*A61M 1/16* (2006.01)
*A61M 1/36* (2006.01)
(Continued)

(52) U.S. Cl.
CPC .......... *A61M 1/1678* (2013.01); *A61M 1/14* (2013.01); *A61M 1/34* (2013.01); *A61M 1/3659* (2014.02);
(Continued)

(58) Field of Classification Search
CPC ...... A61M 25/02; A61M 1/3659; A61M 1/14; A61M 1/1689; A61M 1/1698; A61M 1/26;
(Continued)

(56) References Cited

U.S. PATENT DOCUMENTS 5,800,454 A    9/1998    Jacobsen et al.
6,749,344 B2   6/2004    Hamm et al.
(Continued)

OTHER PUBLICATIONS

International Search Report and Written Opinion issued in corresponding PCT International Application No. PCT/US2019/065954, dated Mar. 19, 2020, pp. 1-14.
(Continued)

*Primary Examiner* — Philip R Wiest
(74) *Attorney, Agent, or Firm* — The Belles Group, P.C.

(57) ABSTRACT

An endovascular apparatus comprises a catheter shaft constructed and designed for insertion into a venous vessel of a patient; a capture thread positioned in at least one lumen of the catheter shaft and extending from a proximal end of the catheter shaft to a distal end of the catheter shaft for capturing components of a bodily fluid from the patient, the catheter shaft including a plurality of ports for exposing the capture thread to the bodily fluid of the patient; and an enclosure coupled to the proximal end of the catheter shaft. The enclosure includes a feed vessel in communication with a first end of the capture thread and a collection vessel in communication with a second end of the capture thread; and a drive system that controls a movement of the capture thread in the catheter shaft from the feed vessel to the collection vessel.

20 Claims, 17 Drawing Sheets

Related U.S. Application Data

(60) Provisional application No. 62/924,834, filed on Oct. 23, 2019, provisional application No. 62/778,732, filed on Dec. 12, 2018.

(51) Int. Cl.
*A61M 1/14* (2006.01)
*A61M 1/34* (2006.01)
*A61M 25/02* (2006.01)

(52) U.S. Cl.
CPC ..... *A61M 25/02* (2013.01); *A61M 2025/0206* (2013.01); *A61M 2025/0213* (2013.01); *A61M 2025/0253* (2013.01)

(58) Field of Classification Search
CPC .............. A61M 1/262; A61M 1/34; A61M 2025/0206; A61M 2025/0213; A61M 2025/0253; A61M 1/16; A61M 1/1678
See application file for complete search history.

(56) References Cited

U.S. PATENT DOCUMENTS

| | | | |
|---|---|---|---|
| 8,157,747 B2 | 4/2012 | Grata et al. | |
| 8,734,382 B2* | 5/2014 | Frankowski | A61M 1/26 |
| | | | 604/26 |
| 2005/0276727 A1* | 12/2005 | Pawliszyn | A61B 5/417 |
| | | | 422/537 |
| 2006/0264810 A1* | 11/2006 | Hattier | B01D 63/02 |
| | | | 604/26 |
| 2009/0227976 A1 | 9/2009 | Calabria et al. | |
| 2015/0335415 A1 | 11/2015 | Batiste | |

OTHER PUBLICATIONS

Sanchez JJ, et al. Neuromonitoring with microdialysis in severe traumatic brain injury patients. Acta Neurochir Suppl. 2013;118:223-7.

Ao X, et al. Enhanced microdialysis relative recovery of inflammatory cytokines using antibody-coated microspheres analyzed by flow cytometry. Anal Chem. Jul. 1, 2004;76(13):3777-84.

McLeod, B.C., Therapeutic apheresis: history, clinical application, and lingering uncertainties. Transfusion. Jul. 2010;50(7):1413-26.

Maitta, R.W., Current state of apheresis technology and its applications. Transfus Apher Sci. Oct. 2018;57(5):606-613.

Twardowski, Z.J., History of hemodialyzers' designs. Hemodial Int. Apr. 2008;12(2):173-210.

\* cited by examiner

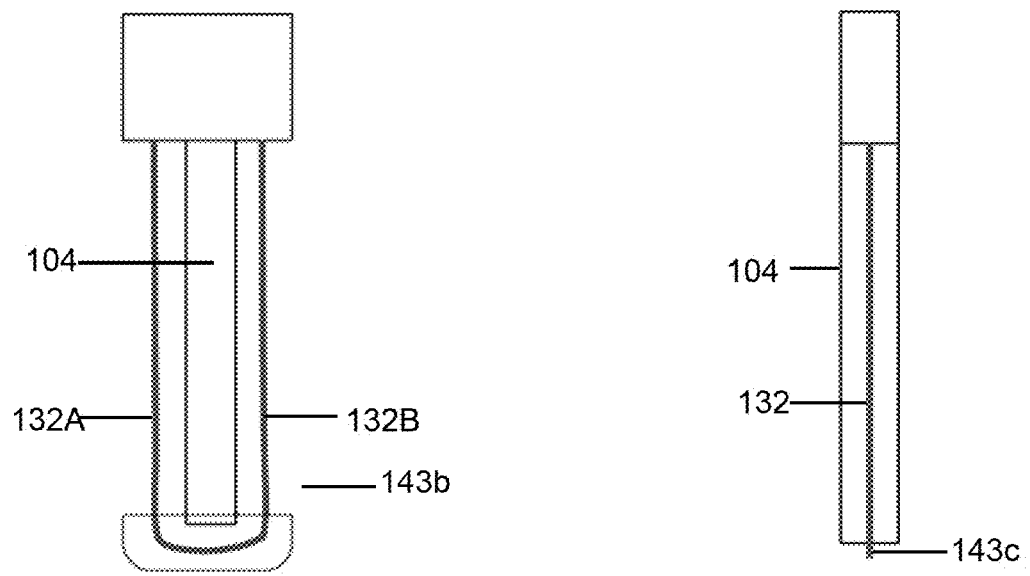
FIG. 2C
FIG. 2D
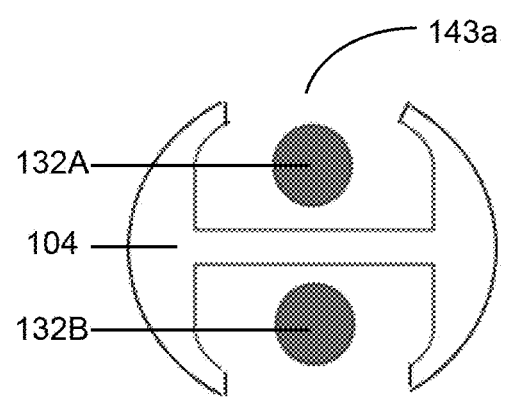
FIG. 2E

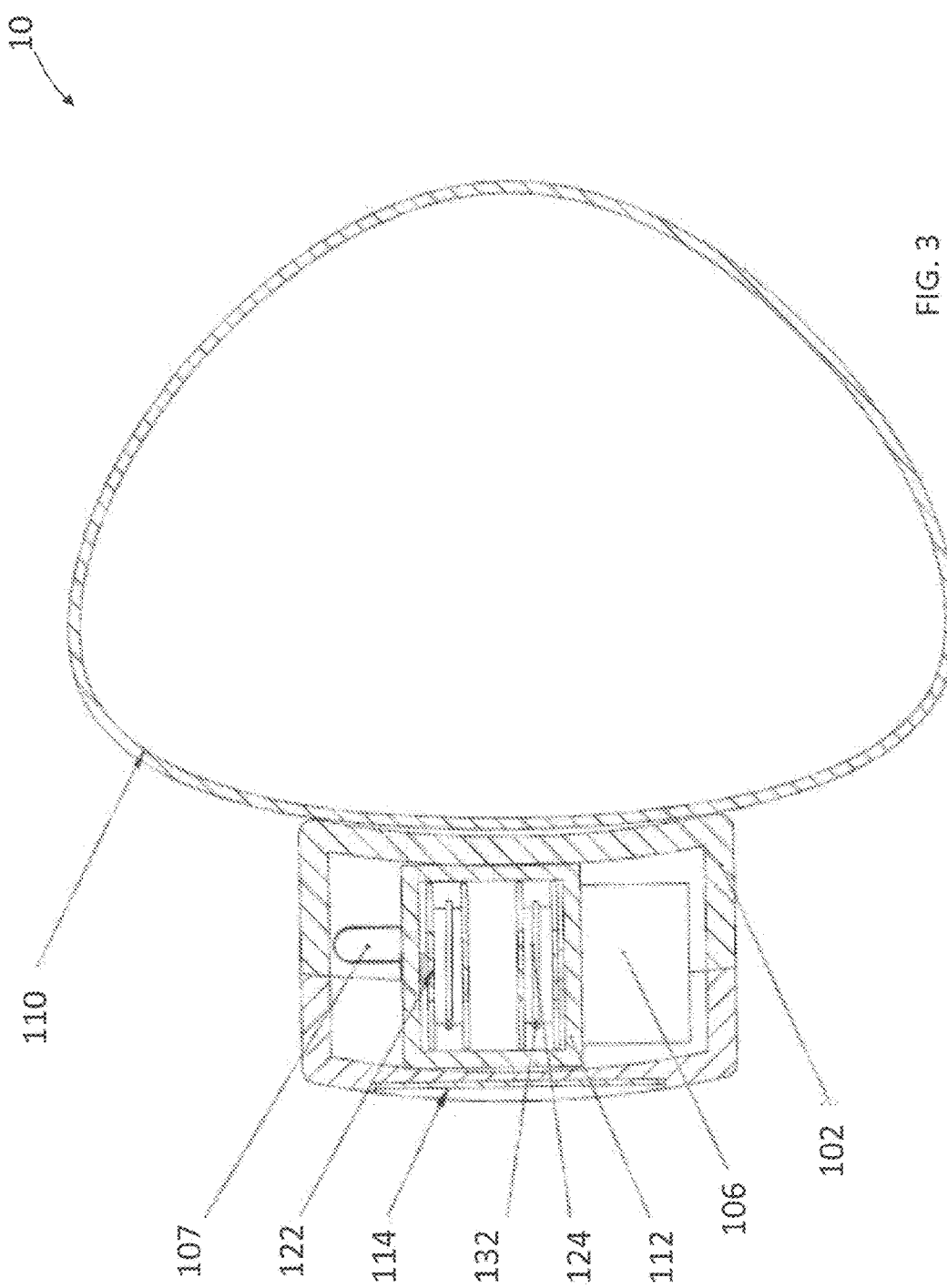

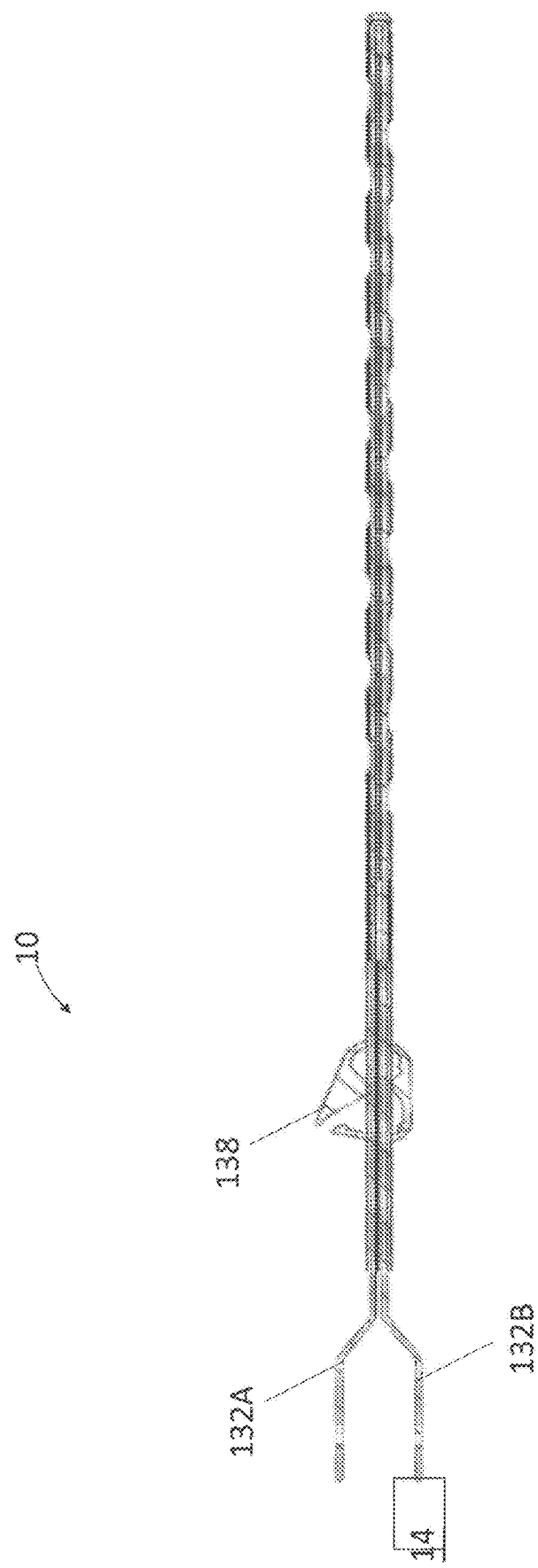

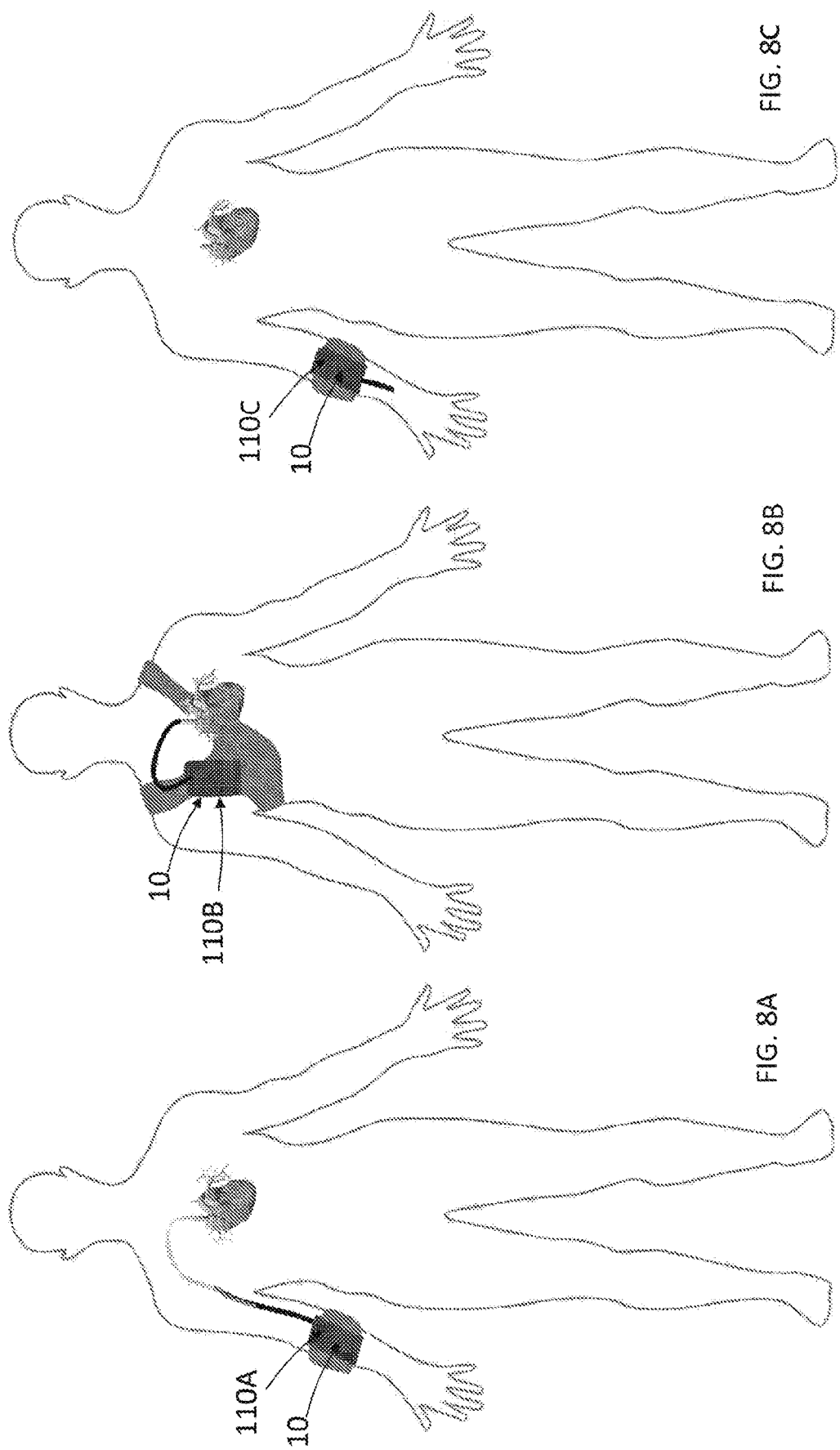

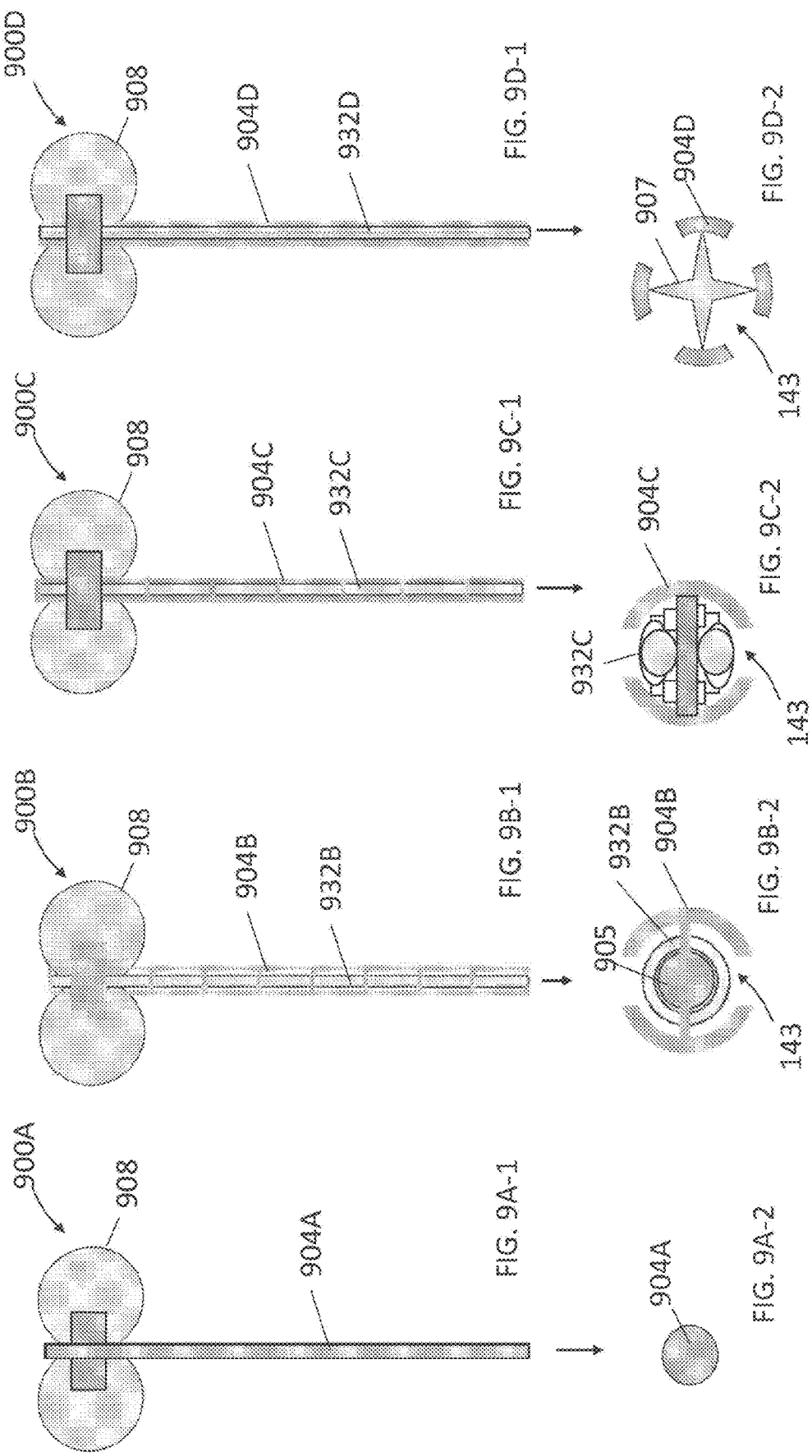

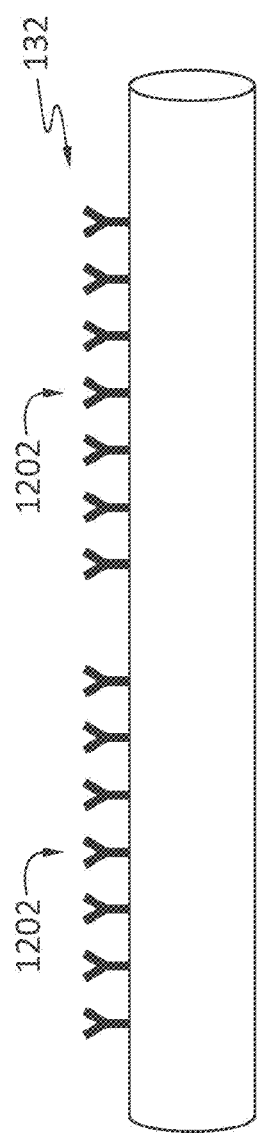
FIG. 12
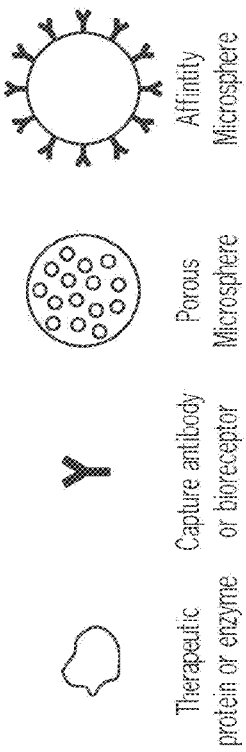
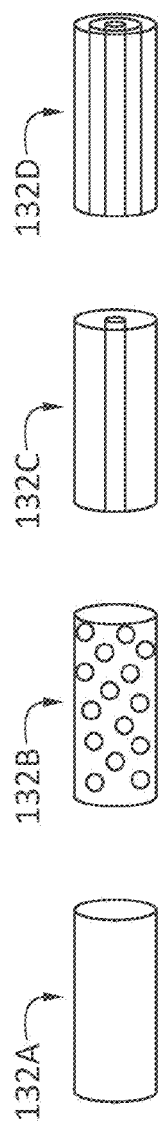
FIG. 13A  FIG. 13B  FIG. 13C  FIG. 13D
FIG. 13E  FIG. 13F  FIG. 13G  FIG. 13H

FIG. 16

| Set Speed (in/min) | Measured Distance (in) | Measured Time (min) | Calculated Speed (in/min) | % Error |
|---|---|---|---|---|
| 0.0236 | 0.1 | 4.0330 | 0.0248 | 5% |
| 0.236 | 1 | 4.1500 | 0.2410 | 2% |
| 2.36 | 6 | 2.4167 | 2.4828 | 5% |
| 11.8 | 12 | 1.0167 | 11.8033 | 0% |
| 23.6 | 12 | 0.6000 | 20.0000 | 15% |

FIG. 17

| Set Speed (in/min) | Deflection at Distal Tip (mm) |
|---|---|
| 0.0236 | 0.8 |
| 0.236 | 0.8 |
| 2.36 | 0.8 |
| 11.8 | 5 |
| 23.6 | 8 |

FIG. 18

| Set Speed (in/min) | Time at Speed (seconds) | Leakage (grams) |
|---|---|---|
| 0.0236 | 60 | 0 |
| 0.236 | 60 | 0 |
| 2.36 | 60 | 0 |
| 11.8 | 60 | 0 |
| 23.6 | 60 | 0 |

# MULTIPURPOSE WEARABLE ENDOVASCULAR APPARATUS

RELATED APPLICATIONS

This application is a continuation-in-part of PCT Application No. PCT/US2019/065954, filed Dec. 12, 2019, which claims the benefit of U.S. Provisional Patent Application No. 62/778,732, filed Dec. 12, 2018, entitled "WEARABLE ENDOVASCULAR APPARATUS FOR CAPTURE/REMOVAL OF BLOOD COMPONENTS, BLOOD OXYGENATION, AND REAL-TIME PATIENT MONITORING" and U.S. Provisional Patent Application No. 62/924,834, filed Oct. 23, 2019, entitled "WEARABLE ENDOVASCULAR APPARATUS FOR CAPTURE/REMOVAL OF BLOOD COMPONENTS, BLOOD OXYGENATION, AND REAL-TIME PATIENT MONITORING," the contents of each of which are incorporated herein by reference in their entirety.

TECHNICAL FIELD

The present inventive concepts generally relate to the field of medical devices for the treatment and/or monitoring of a patient's blood, and more particularly, to a multi-purpose wearable medical device that performs one or more of a blood filtration, endovascular oxygenation, endovascular and tissue monitoring, and the capture or removal of bodily fluid components for detoxification, analysis, or other medical purposes.

BACKGROUND

Modern blood filtration devices such as hemodialysis and therapeutic apheresis machines have major drawbacks. In particular, these machines are large, complex, and expensive, difficult to use and maintain, and require patients to endure long, time-consuming treatments. These machines are large at least in part because of the complexities associated with hemodialysis and therapeutic apheresis treatments that require blood to be drawn from the patient's body, filtered by the machine external to the body, and returned by the machine to the body. Hemodialysis machines treat chronic kidney disease or end-stage renal failure by performing treatments for several hours per session and for several days per week in order to remove excess water, solutes, and uremic toxins from the blood. Similarly, therapeutic apheresis machines remove a range of undesirable blood components such as cryoglobulins, autoantibodies, LDL cholesterol, immune complexes, endotoxins, and others, but require periodic and long (up to four hours) patient treatment sessions.

However, complications can occur in patients undergoing a hemodialysis or therapeutic apheresis procedure, such as hypotension, hypocalcemia, seizures, vomiting, volume overload, cardiac arrythmia, or sudden cardiac death. Complications related to the use of hemodialysis or apheresis machines are significantly elevated in pediatric and neonatal patients. These machines are not designed for pediatric use and can easily dehydrate and kill a patient if proper adjustments are not made. Specialized centers with highly trained professionals are required for performing neonatal hemodialysis or apheresis. Age can be a main factor in the injury or death of children while undergoing these treatments using these machines. Another disadvantage of these machines is that uncomfortable arteriovenous fistulas or grafts typically have to be placed in a patient's arm as a portal to pump blood from the body, and can cause clotting or other undesirable effects on the body.

Conventional non-therapeutic devices such as microdialysis and open-flow microperfusion devices can perform a minimally-invasive sampling technique that includes the continuous analysis of extracellular fluid of organs such as the brain, heart, skeletal muscle, skin, and others. In a microdialysis procedure, a probe is covered with a dialysis membrane, or filter, at the desired molecular weight cutoff to allow for the passive diffusion of molecules from the extracellular space. An aqueous solution is perfused through the probe at a low flow rate, allowing for the continuous sampling and monitoring of the organ's extracellular environment in normal or pathological conditions. Microdialysis has been used to quantitate molecules, which range from small molecules such as glutamate, acetylcholine, serotonin, and dopamine to larger molecules such as neuropeptides, growth factors, and extracellular cytokines, and has therefore become a valuable technique for understanding disease mechanisms and the microenvironment.

Neuromonitoring with microdialysis systems has the potential for early detection of complications with traumatic brain injuries by monitoring the glucose and lactate levels in the brain, for example, described in an article published by Sanchez J J, et al., entitled "Neuromonitoring with microdialysis in severe traumatic brain injury patients," Acta Neurochir Suppl. 2013; 118:223-7, the contents of which are incorporated herein in their entirety. However, microdialysis probes are limited in their macromolecule samplings with a molecular weight cutoff of 3000 kDa. Additionally, when using a microdialysis system, there is a slow diffusion of the extracellular fluids resulting in low recovery rate. In order to enhance the recovery rate, antibody-coated microspheres were evaluated in the perfusate, which led to an enhanced diffusive driving force and increased recovery, for example, described in an article published by Ao X, et al., entitled "Enhanced microdialysis relative recovery of inflammatory cytokines using antibody-coated microspheres analyzed by flow cytometry," Anal Chem. 2004 Jul. 1, 76(13):3777-84, the contents of which are incorporated herein in their entirety.

Another conventional approach for overcoming the challenges associated with sampling high molecular weight analytes or highly lipophilic molecules is a non-membrane-based sampling technique, referred to as an open-flow micro-perfusion. Here, a probe is embedded with macroscopic holes without any dialysis membrane covering its surface. A push-pull pump system is used to push the perfusate into the probe and remove it using the second pump. This provides a diluted, non-filtered sample with a longer sampling time that similar to a microdialysis technique in that it can be directly measured in real-time using analytical techniques.

A point-of-care system developed for microdialysis procedures performed on intensive care patients is the ISCUS Flex microdialysis analyzer, which can monitor up to eight patients simultaneously to detect a brain ischemia and metabolic crisis. This analyzer can analyze brain tissue glucose, lactate, glycerol, pyruvate, urea, and glutamate levels at a rate of about 30 measurements per hour. However, conventional microdialysis and open-flow microperfusion systems described above are not practical for blood filtration and biosensor-based monitoring purposes due to dialysis membrane fouling, leakage of the perfusate, or low capture rate complications.

Extracorporeal membrane oxygenation (ECMO) systems are used to provide oxygen delivery for cardiac and/or respiratory failure patients. However, ECMO systems require the step of pumping blood out of the body to allow for oxygenation through gas exchangers. There are several complications that can occur as a result of ECMO, including neurologic complications such as intracerebral or subarachnoid hemorrhages, ischemic infarctions, coma and brain death, due to the infused anti-coagulants and platelet dysfunction. Heparin-induced thrombocytopenia can also occur as result of the infused heparin anticoagulant, which can increase the risk of thrombosis. Children are particularly prone to the greatest risk of complications due to ECMO. For example, preterm infants are at a very high risk of developing an intraventricular hemorrhage which subjected to an ECMO procedure.

While the foregoing conventional systems have non-therapeutic uses, there are currently no endovascular blood filtration products available on the market for the therapeutic intervention of acute or chronic pathological conditions. Furthermore, given the size, cost, and complexity of these machine-based systems, they are limited for use in hospitals or treatment centers. Accordingly, for at least the foregoing reasons, a new approach is needed for the capture or removal of blood components, blood oxygenation, and real-time patient monitoring.

SUMMARY

In one aspect, an endovascular apparatus is constructed and arranged as a blood filtration apparatus by including a source of capture thread extending through a catheter shaft, and that rotates inside the catheter shaft between a feed vessel and a collection vessel. When the catheter shaft is inserted in a blood vessel such as a vein, the capture thread is exposed to a user's blood. The blood is filtered by the capture thread which captures and/or removes blood components of interest such as lipids, nucleic acids, stem cells, cancer cells, pathogens, and so on as the blood passes openings in the catheter that expose the blood to the capture thread inside the catheter shaft.

In some embodiments, an endovascular apparatus is constructed and arranged as an endovascular oxygenation device that includes a catheter shaft and capture thread, and further includes an oxygenator at a proximal end of the shaft that receives a source of capture thread that rotates, translates, and/or otherwise moves between the catheter shaft and the oxygenator when outputting oxygen to the user's blood vessel, removing carbon dioxide from the user's blood, and/or performing a related oxygenation procedure.

In some embodiments, an endovascular apparatus is constructed and arranged as a monitoring apparatus that can provide point-of-care monitoring of patients by capturing metabolites and biomarkers through the capture thread and quantifying them in a bioanalyzer or the like. The analysis can be performed in real-time or near real-time for patient monitoring during the endovascular blood filtration treatment, tissue monitoring for traumatic brain injury patients, or as standalone point-of-care system for intensive and critical care patients as well as high-risk long-term care settings.

In some embodiments, a static capture endovascular apparatus is constructed and arranged as a catheter, or probe or the like, for the rapid capture and removal or detoxification of undesirable molecules for treatment of range of acute pathological conditions. Here, a static, non-rotating capture thread is incorporated instead of a rotatable capture thread device where a long-term and extensive capture is not required. The rapid capture probe is beneficial in neonatal and pediatric patients who have small and hard to access vasculature.

In one aspect, an endovascular apparatus comprises a catheter shaft constructed and designed for insertion into a patient; a capture thread positioned in at least one lumen of the catheter shaft and extending from a proximal end of the catheter shaft to a distal end of the catheter shaft for capturing bodily fluid components from the patient, the catheter shaft including a plurality of ports for exposing the capture thread to the bodily fluid in the patient; and an enclosure coupled to the proximal end of the catheter shaft. The enclosure includes a feed vessel in communication with a first end of the capture thread and a collection vessel in communication with a second end of the capture thread; and a drive system that controls a movement of the capture thread in the catheter shaft from the feed vessel to the collection vessel.

In some embodiments, the endovascular apparatus further comprises a strap coupled to the enclosure for removably and wearably coupling the enclosure to a chest or arm of the patient so that the catheter shaft is in proximity of a venous region.

In some embodiments, the catheter shaft includes a plurality of ports that expose the capture thread to the bodily fluid in a venous vessel.

In some embodiments, the components of the bodily fluid include a combination of non-cellular and cellular blood components.

In some embodiments, the non-cellular blood components include one or more of proteins, lipoproteins, lipids, nucleic acids, small molecules, and carbohydrates, and the cellular components include one or more of hematopoietic stem cells, mesenchymal stem cells, progenitor cells, immune cells, cancer cells, and pathogens.

In some embodiments, the endovascular apparatus is constructed and arranged as a blood processing device, wherein the capture thread includes a hollow capture thread coated with an ultrafiltration material that captures components of interest from the blood.

In some embodiments, the endovascular apparatus is constructed and arranged as areal-time monitoring device, wherein the capture thread captures metabolites and biomarkers of the components of the bodily fluid for output to an external analysis machine.

In some embodiments, the bodily fluid includes brain tissue for monitoring.

In some embodiments, the endovascular apparatus is constructed and arranged for insertion into a venous region or other hole or lumen of the patient.

In some embodiments, the capture thread removes carbon dioxide from the bodily fluid and is also coated with an oxygenation material that adds oxygen to the bodily fluid.

In some embodiments, the enclosure includes at least one access port that provides access by an external device to the capture thread.

In some embodiments, the endovascular apparatus further comprises a check valve at the catheter shaft that prevents the bodily fluid from entering the feed vessel and the collection vessel.

In some embodiments, the endovascular apparatus further comprises a safety lock that limits a flow and movement of any liquid, air, or the capture thread.

In some embodiments, the endovascular apparatus further comprises a distal tip guide about which the capture thread is positioned, and rotates about from the feed vessel to the collection vessel.

In another aspect, a medical oxygenation apparatus comprises endovascular apparatus comprises a catheter shaft constructed and arranged for insertion into a venous vessel of a patient; and an oxygenation thread extending from a proximal end of the catheter shaft to a distal end of the catheter shaft for oxygenation of blood from the venous vessel of the patient as the capture thread, and a drive for driving the thread. The medical oxygenation apparatus further comprises an oxygenator, the thread extending through a chamber of the oxygenator, which oxygenates the thread and removes carbon dioxide from the capture thread; and a blender that outputs a desired fraction of delivered oxygen to the chamber of the oxygenator for oxygenating the thread.

In some embodiments, the medical oxygenation apparatus further comprises an enclosure coupled to the proximal end of the catheter shaft, the enclosure including a feed vessel in communication with a first end of the capture thread; a collection vessel in communication with a second end of the capture thread; and a drive system that controls a movement of the capture thread in the catheter shaft from the feed vessel to the collection vessel.

In another aspect, an endovascular apparatus for capturing undesirable molecules, comprises a static catheter shaft constructed and arranged for insertion into a venous vessel of a patient; and a capture element in communication with the static catheter shaft for capturing or detoxifying components of a bodily fluid from the venous vessel of the patient.

In some embodiments, the static catheter shaft comprises a cylindrical rod and the capture element includes antibodies, proteins, peptides, chelators, enzymatic moieties, and others that are coated on the cylindrical rod.

In some embodiments, the static catheter shaft includes a hollow interior that receives a mandrel, and wherein the capture element comprises a capture thread about the mandrel.

In some embodiments, the static catheter shaft includes a hollow interior, wherein the capture element comprises a capture thread is stitched to the hollow interior of the catheter shaft.

In some embodiments, the catheter shaft includes a hollow interior, and wherein the capture element comprises a star-shaped core positioned in the hollow interior of the catheter shaft. In another aspect, an endovascular apparatus comprises a catheter shaft constructed and arranged for insertion into a venous vessel of a patient; a capture thread positioned in at least one lumen of the catheter shaft and extending from a proximal end of the catheter shaft to a distal end of the catheter shaft for capturing components of a bodily fluid from the venous vessel of the patient as the capture thread rotates inside the catheter shaft, the catheter shaft including a plurality of ports for exposing the capture thread to the venous vessel; and an outlet for transferring the capture thread including the captured components of the bodily fluid to an external analysis machine.

In another aspect, an endovascular apparatus, comprises: a catheter shaft constructed and arranged for insertion into a patient; a capture thread positioned in at least one lumen of the catheter shaft and extending through the catheter shaft from a proximal position of the catheter shaft to a distal position of the catheter shaft and returning to the proximal position of the catheter shaft, the capture thread constructed and arranged to capture components of a bodily fluid from the patient, the catheter shaft including at least one port exposing the capture thread to the bodily fluid of the patient; and an enclosure coupled to the proximal end of the catheter shaft. The enclosure includes: a feed vessel in communication with a first end of the capture thread; a collection vessel in communication with a second end of the capture thread; and a drive system that controls a movement of the capture thread in the catheter shaft from the feed vessel to the collection vessel.

In some embodiments, the drive system controls movement of the capture thread in a distal direction from the proximal position to the distal position and in a proximal direction from the distal position to the proximal position.

In some embodiments, the feed vessel provides a source of capture thread.

In some embodiments, the feed vessel comprises a spool for seating the source of capture thread.

In some embodiments, the capture vessel collects returned capture thread having been exposed to the bodily fluid of the patient.

In some embodiments, the capture vessel comprises a spool for seating the returned capture thread.

In some embodiments, the drive system controls a rotation of the spool about an axis of the spool for pulling the capture thread through the catheter shaft.

BRIEF DESCRIPTION OF THE DRAWINGS

The present inventive concepts are illustrated by way of example and is not limited by the accompanying figures, in which like references indicate similar elements. Elements in the figures are illustrated for simplicity and clarity and have not necessarily been drawn to scale.

FIGS. 2B-2E are views of the wearable endovascular apparatus of FIG. 1 in accordance with a second embodiment.

FIG. 3 is a cross-sectional view of the wearable endovascular apparatus of FIG. 1.

FIG. 7 is a cross-sectional view of a wearable endovascular apparatus communicating with a biomarker analyzer, in accordance with some embodiments.

FIG. 8A is an illustrative view of a central venous catheter at a basilic vein of a user, in accordance with some embodiments.

FIG. 8B is an illustrative view of a peripherally inserted central catheter located at a subclavian vein of a user, in accordance with some embodiments.

FIG. 8C is an illustrative view of a peripheral venous catheter located at peripheral vein in the wrist of a user, in accordance with some embodiments.

FIGS. 9A-1 and 9A-2 are top and front views, respectively, of a static endovascular probe, in accordance with some embodiments.

FIGS. 9B-1 and 9B-2 are top and front views, respectively, of a static endovascular probe, in accordance with other embodiments.

FIGS. 9C-1 and 9C-2 are top and front views, respectively, of a static endovascular probe, in accordance with other embodiments.

FIGS. 9D-1 and 9D-2 are top and front views, respectively, of a static endovascular probe, in accordance with other embodiments.

FIG. 12 is a side view of an endovascular thread coated with various capture moieties, in accordance with some embodiments.

FIGS. 13A-13H are side views of various capture thread configurations, in accordance with some embodiments.

FIGS. 16-18 are tables including measurement data of a wearable endovascular apparatus of FIG. 1, in accordance with some embodiments.

DETAILED DESCRIPTION

Figure 1:
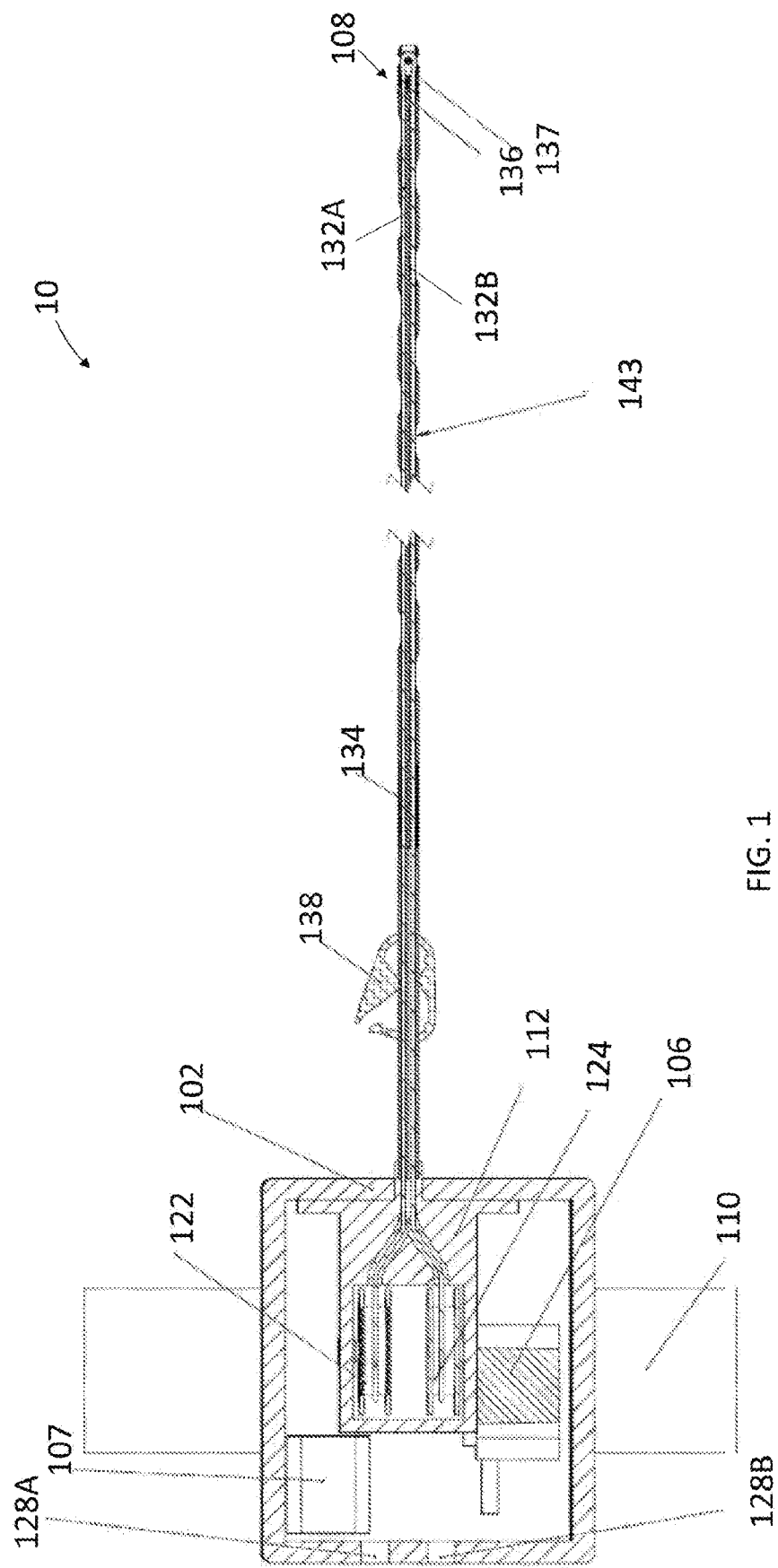
FIG. 1 is a cross-sectional side view of a wearable endovascular apparatus, in accordance with some embodiments.

In brief overview, embodiments of the present inventive concepts include multipurpose wearable medical apparatuses, systems, and methods that are versatile, cost-effective, and patient-friendly for treating a range of acute and chronic pathological conditions, for example, as described in detail below, for blood oxygenation of patients with cardiovascular and pulmonary complications, and for real-time monitoring of high-risk patients. A patient may be a human or an animal or other organism. The endovascular apparatus is constructed and arranged to perform one or more different functions, including but not limited to blood filtration, endovascular oxygenation, endovascular and tissue monitoring, and bodily fluid component capture and removal. To perform these functions, the endovascular apparatus includes a capture thread inside a catheter shaft that selectively captures the non-cellular and cellular components for the treatment of a range of acute and chronic pathological conditions, provides intravascular oxygenation of patients with cardiovascular and pulmonary complications in need of acute or chronic systemic oxygenation, and/or performs real-time monitoring of metabolites and biomarkers of a patient. When describing various treatments performed according to the inventive concepts, such treatments may refer to medical care including the administration of drugs, diagnostics, delivery or removal of bodily fluids, therapeutics or patient.

Some examples of undesirable blood components to be removed using embodiments of the inventive endovascular apparatus can be for the treatment of various diseases, and can include but not limited to cryoglobulins, immunoglobulins, autoantibodies, LDL cholesterol, lipoproteins, lipids, cytokines, immune complexes, endotoxins, bacterial toxins, amino acids, ammonia, carbohydrates, drugs, chemotherapeutic agents, uremic toxins, activated complement, von Willebrand factor, clotting factors, free hemoglobin, IV imaging contrast agents, infectious pathogens, chemical toxins, metals, metabolites, reactive oxygen species, advanced glycation end products, oxidized blood components, amyloid proteins, nucleic acids, and a range of small molecules and proteins. Some examples of cellular components that can be removed using the inventive endovascular apparatus for diagnostic and therapeutic purposes include hematopoietic stem cells, mesenchymal stem cells, progenitor cells, immune cells, cancer cells, red blood cells, platelets, and pathogens. The endovascular apparatus in accordance with some embodiments is used for the treatment of cytokine storms resulting from septic shock, trauma, and autoimmune diseases, elevated LDL cholesterols from familial hypercholesterolemia patients, autoimmune diseases, drug abuse or overdose, acute and end-stage renal disease, hemochromatosis, hemoglobinopathies, hyperammonemia, hyperargininemia, amyloidosis, pre-eclampsia, cancers, bacteremia, viremia, fungemia, infectious diseases, for military applications for treating injured soldiers in battlefield contaminated with toxic chemicals or infectious pathogens, and range of other applications. Non-cellular blood components may include by way of example, but not be limited to proteins, lipoproteins, lipids, nucleic acids, small molecules, and carbohydrates, as well as cellular components, e.g. hematopoietic stem cells, mesenchymal stem cells, progenitor cells, immune cells, cancer cells, and pathogens. Accordingly, the endovascular apparatus can selectively capture of non-cellular or cellular components. In other embodiments, an endovascular apparatus captures stem cells, progenitor cells or other circulating cell types for treatment of autoimmune diseases, cardiovascular diseases, neurodegenerative diseases, trauma, stroke, genetic disorders and others.

The cellular and non-cellular components captured by the endovascular apparatus may pertain to human or non-human sources, for example, land and aquatic animals. These include biological products such as proteins, cells, vaccines, and other blood components. One example of an animal-based application is the safe removal of amebocytes from horseshoe crabs instead of the current direct blood harvest that can result in a 30% mortality rate and unclear recovery rate for the released surviving crabs. The captured components can pertain to protein production cultures and bioreactors containing bacteria, yeast, algae filamentous fungi, insect cells, or mammalian cells for the purposes of capture and real-time monitoring.

In some embodiments, a wearable endovascular apparatus configured as a blood filtration device is used to treat a range of pathological complications such as cytokine storms resulting from septic shock, trauma, and autoimmune diseases, elevated LDL cholesterol from familial hypercholesterolemia patients, autoantibodies in autoimmune diseases, drug overdose, chemotherapeutic agents, uremic toxins, as well as military applications for treating injured soldiers in battlefield contaminated with toxic chemicals or infectious pathogens. Here, the endovascular blood and plasma filtration device can provide an easy-to-use, non-extracorporeal, widely accessible, patient-friendly alternative to hemodialysis or therapeutic apheresis machines. In these embodiments, the device allows for the ability to have a longer treatment duration at less complexity than the abovementioned conventional machines used to treat such conditions.

As mentioned above, the multipurpose endovascular apparatus in some embodiments operates as an oxygenation system for the treatment of patients with functioning circulatory systems who are not able to oxygenate for example due to respiratory failure, lung transplantation, airway obstruction, acute respiratory distress syndrome, pulmonary hemorrhage, as well as for aiding in cardiac support such as in cardiomyopathy, myocarditis and cardiac depression. The oxygenation features of the device remove carbon dioxide ($CO_2$) from the blood while simultaneously adding oxygen through techniques such as oxygenated hemoglobin and carbonic anhydrase. This endovascular oxygenation device avoids the use of anticoagulants such as heparin which is known to cause neurological complications and immune-induced thrombosis through heparin-induced thrombocytopenia. Endovascular oxygenation also avoids the need for conventional blood pumps for extracorporeal oxygenation, which are prone to complications in children.

As also mentioned above, the multipurpose endovascular apparatus in some embodiments operates as a real-time or near real-time monitoring device, which can be used for biosensor devices for the point-of-care monitoring of patients in conjunction with other treatments or stand-alone treatments. The multipurpose endovascular apparatus may comprise a microdialysis probe and the endovascular apparatus may be referred to as a microdialysis apparatus. The microdialysis probe may be similar in structure to the catheter which is described herein. In one embodiment, the microdialysis probe comprises a catheter and an interior rotating thread. The rotating thread may be made from any thin, strong material such as silk. As previously described, the rotating thread materials may be coated with a capture material. In a preferred embodiment, the microdialysis probe would function without the use of a perfusate and without the incorporation of a membrane portion. This overcomes the diffusion and capture challenges faced by microdialysis devices, as the present invention has free access to liquids in the tissue that it is placed in and has greater capture capacity of molecules of any size or physicochemical properties. The present invention can be used for real-time analysis of tissue.

It should be noted that the thread of the device can feed into a diagnostic analyzer device or near real-time patient monitoring of a range of molecules, small and large, and should not be read as to be limited to the molecular cutoffs of standard microdialysis machines or the like. Diagnostic threads with designated biomarker detection regions can capture the analyte of interest, and quantify it through electrochemical and/or optical sensors in the analyzer device. The biosensor can continuously analyze bodily fluid, blood as well as extracellular fluid and the local environment of organs such as brain, heart, skeletal muscle, skin, and others. Various physical and chemical properties can be monitored in addition including but not limited to the temperature of the local environment and pharmacokinetics. A monitoring device according to embodiments of the inventive concepts is minimally-invasive, thereby allowing real time monitoring of areas of the body such as the brain, for a longer duration with minimal disruption of a patient's normal routine thus allowing for a new technique to monitor a brain injury.

In some embodiments, a rapid endovascular capture probe captures undesirable molecules. In particular, the endovascular static capture probe allows for the rapid short-term capture and removal of desired undesirable molecules. This is particularly beneficial for short-term acute disease applications, where longer threads are not required. This can include the capture of a range of small and large molecules, for a range of acute pathological conditions, such as hyperammonemia, hyperbilirubinemia, hemoglobinemia, hemochromatosis, hyperkalemia, drug overdose, heavy metal poisoning, contrast-induced nephropathy, nephrogenic systemic fibrosis, azotemia, septicemia, and others. One key advantage of the rapid endovascular capture probe in accordance with embodiments is that it can be very narrow in diameter, for example, 1-7 FR but not limited thereto, allowing for insertion into small vessels such as in a user's wrist. This is especially useful for neonatal and pediatric patients who have small and hard to access veins. The static capture thread can be shielded by a catheter shaft or freely accessible in the vasculature. A mandrel provides rigidity for the thread to enable insertion into the vessel. This can be particularly helpful for pediatric pathological conditions, where such as pediatric hemodialysis machines and access to highly trained physicians are not available. The static rapid endovascular capture probe can be used for removal of range of molecules in neonatal, pediatric, and adult patients.

Other embodiments of the wearable endovascular apparatus include a hemodynamic filtration catheter that captures various body fluids, such as water or plasma. A segment of the device directs blood flow towards the base of the catheter that is covered with a membrane, such as a polysulfone membrane (different pore sizes for removal of water or plasma). In some embodiments, the multiple segments can be angled, whereby the angled segments would create pressure on the dialysis membrane to push the water or plasma across into the empty region that collects into a collection bag.

Referring to FIGS. 1-3, some embodiments of a multipurpose wearable endovascular apparatus 10 include a catheter shaft 104, capture thread 132, a catheter or probe tip 108, an electronic display 114, and a housing 102 (also referred to as an enclosure) that encloses one or more of a drive system 106, a feed vessel 122, a collection vessel 124, and/or various electrical and electro-mechanical components described in detail below.

The catheter shaft 104 can be constructed and arranged as a central venous catheter (CVC), peripherally inserted central line catheter (PICC), or other probe construction that is suitable for a particular patient's vein in the wrist, arm, leg, or large veins in the chest, for example, ranging from larger veins such as subclavian or jugular veins to smaller veins such as a basilic vein. For example, as shown in FIG. 8B, the endovascular apparatus 10 can be constructed and arranged as a central venous catheter that can be located at a subclavian vein, jugular vein, or other large venous vessel of the body, in accordance with some embodiments. Alternatively, as shown in FIGS. 8A and 8C, the endovascular apparatus 10 can be constructed and arranged as a catheter that can be peripherally inserted at a smaller vein, such as a basilic vein. In other embodiments, the endovascular apparatus 10 can be constructed and arranged as a peripheral venous catheter inserted into a vein in the wrist (See FIG. 8C). In certain embodiments, the endovascular apparatus 10 of FIG. 8C is a microdialysis probe. The size and site of the venous region of the patient determines the flow rate suitable for the endovascular apparatus 10. Various catheter dimension ranges are mentioned herein, but not limited thereto. Factors determining the vein dimensions, and therefore the endovascular probe size, may include the age or size of the patient. For example, the probe size for a large vein a pediatric patient's chest may range from 4-7 FR, and a PICC line catheter in an arm vein may range from 3-5 FR, or in some embodiments less than 3 FR, or in other embodiments less than 1 FR. In adult patients, a central line catheter diameter may be greater than 7 FR for large veins, and less than 7 FR for PICC catheters. Generally, an endovascular probe catheter diameter is one-third to one-half the diameter of the selected venous vessel, but not limited thereto. In some embodiments, the catheter shaft 104 is constructed and arranged to include a single lumen, dual lumen or multi-lumen while configured to be sufficient for vascular port access or direct entry to a venous region. In some embodiments, the catheter shaft 104 can be constructed and arranged for insertion into a lumen or orifice other than a vein or artery. For example, the endovascular apparatus 10 may be inserted into a patient's brain for collecting brain tissue via a hole drilled through the patient's skull, the patient's naval cavity, or ear.

The catheter shaft 104 can be formed of polyurethane such as thermoplastic polyurethane (TPU), silicone, Pebax, or another polymer or Class VI material conducive to a predetermined use or application of the endovascular apparatus 10 depending on catheter size and insertion length based on patient size and site of access to a patient's vascular system. The catheter shaft 104 may comprise other materials such as any medical grade short-term or long-term implantable polymer. The catheter shaft 104 may also comprise multiple layers including a metal or polymer fiber braid to add stiffness and/or an internal or external lubricious layer. Accordingly, the catheter shaft 104 may exhibit desirable material properties, in particularly, the flexibility or hardness of the shaft 104. For example, the durometer of the catheter shaft 104 may be in the range of 10-90 Shore D. In some embodiments, the durometer at all points along the catheter shaft axis may not be uniform due to components internal or external to the shaft 104, bond joints, and distal end components. Optimizing a catheter shaft durometer is important because an increase in hardness may correspond to decreased comfort for the patient but will provide additional structure to prevent kinking as the capture thread 132 rotates during a medical procedure. The capture thread 132 can be various sizes, and can vary in thickness, width, and length. The configurations of the thread 132 as described herein may establish the requirements necessary for the apparatus 10 to properly function, depending on use and application of the endovascular apparatus 10.

In some embodiments, some or all surfaces of the endovascular apparatus 10, in particular, the feed and collection vessels 122, 124 and the catheter shaft 104 or other surfaces in contact or in proximity of a patient, is coated with an anti-thrombogenic, anti-bacterial material for anti-microbial purposes, and for aiding in a cleaning procedure. In order to prevent any acute or long-term reaction to the thread or rod, the surface may be modified with different immunomodulatory modalities including, but not limited to, CD47 peptides and dual thrombomodulin/EPCR proteins. CD47 is a transmembrane protein that is ubiquitously expressed in human cells and acts as a "don't eat me" signal to allow recognition as "self" to avoid uptake and activation by the innate immune response. It interacts with SIRPα immunoreceptor expressed on macrophages, dendritic cells and granulocytes, leading to inhibition of prophagocytic mechanism. Surface modification of biomaterials with CD47 peptide has been used to mitigate inflammatory response, including both adaptive and innate immune responses. The minimal "self" CD47 peptide is derived from full length CD47 protein. It has successfully been reported to reduce uptake by innate immune cells. Another novel biomaterial surface modification that has been reported to have both anti-inflammatory and anti-thrombotic properties is the thrombomodulin-EPCR system. In order to mimic the endothelial cell surface lining, co-immobilization with thrombomodulin and Endothelial Protein C Receptor (EPCR) has been used demonstrating superior biomaterial protection from thrombosis. Thrombomodulin is known to accelerate activated protein C (APC) production and inhibit thrombin formation, which are key to suppressing intravascular coagulation. Consequently, APC has potent anti-inflammatory properties which have been reported to suppress production of pro-inflammatory cytokines such as IL-6, IL-8, IL-10, and TNF-α. To achieve the greatest APC production, thrombomodulin is co-immobilized with its natural co-factor endothelial cell protein c receptor (EPCR) using a bidentate functional group to bring TM and EPCR in close proximity. As shown by Kador K. E. et al. this process achieves greater APC generation than TM alone. Immobilization of TM on the static catheter, through this unique bidentate conjugation approach with its natural co-factor will allow for maximum APC production.

The catheter shaft 104 could also be constructed from a silver salt or other anti-microbial augmented polymer to prevent microbes or bioburden formation. For long-term use or in cases of contamination of the apparatus 10, a 2% chlorhexidine gluconate solution or other broad-spectrum antimicrobial agent can be used to clean the feed and collection vessels 122, 124 to maintain aseptic conditions. In order, to prevent leakage of chlorhexidine or the like into the blood, a cap (not shown) similar to a hemodialysis catheter cap or the like can be coupled to one or both vessels 122, 124, which include at least some of a spool of the capture thread 132, and only opened for performing a standard in-dwelling catheter cleaning procedure. In other embodiments, a cap is located on one or more access ports 128A, B (generally, 128) of the enclosure 102 for allowing access to the vessels 122, 124, and/or receiving a source of capture thread 132. Here, the ports 128 can provide an interface to an ancillary device with respect to incoming capture thread or return capture thread. For example, the return capture thread 132B which includes bodily fluid components can be provided via port 128B to a bioanalyzer or other apparatus. In other embodiments, the ports 128A, 128B may provide an interface to the drive system 106, for example, to change settings of the motor to increase or decrease a rate of rotation of the capture thread 132 inside the catheter shaft 104.

In some embodiments, the endovascular apparatus 10 includes a safety lock mechanism 138 or related valve, switch, clamp or the like that is rotated, clamped, or otherwise moved to a closed position to shut off all movement of liquid, air, and capture thread between the housing 102 and catheter shaft 104 if an emergency situation arises, for example, in case of any leak or device malfunction. In some embodiments, the safety lock mechanism 138 is incorporated in the catheter shaft 104 at the site of catheter exit from the patient. The safety lock 138 may be a standard clip or a Tuohy Borst type shut off in line with the catheter shaft 104. For example, at the site of exit from the tissue, there is a gap for placing the catheter into a body lumen or sub-dermally. After the catheter exits the skin, the safety lock 138, similar to a hemostasis valve or Tuohy Borst fitting, functions as an emergency off switch to limit, mitigate, or otherwise prevent some or all flow and movement of any liquid, air, or capture thread by applying a clamp or the like which closes down on the catheter to shut off all movement of liquid, air, and capture thread.

The safety lock mechanism 138 can be part of a cleaning mechanism. Following closure of the safety lock 138, cleaning can occur of the vessels 122, 124 with a chlorhexidine solution or the like, which are then rinsed to remove traces of the antimicrobial agent using a same or similar procedure as that performed in modern hemodialysis catheters. The collection vessel 124 has a retractable reel that is used to collect the capture thread 132 exiting the catheter shaft 104. A coiled spring formed of stainless-steel or other material can expand and contract with thread tension. Retraction can only occur upon the movement initiated by a rotational motor of the drive system 106. The rotational motor and collection/feed vessels 122, 124 are anchored on the arm or the chest using a patient-friendly garment 110 such as a wearable strap or the like, for example, straps 110A, 110B, and 110C shown in FIGS. 8A, 8B, and 8C, respectively. Regardless of shape, size, or configuration of the garment 110, the garment 110 extends from or is otherwise coupled to the housing 102 enclosing the feed/collection vessels 122, 124 and the rotational motor.

In some embodiments, the miniature rotational motor of the drive system 106 is connected to a center of a thread spool in the collection vessel 124 to rotate the collection vessel thread spool thereby winding or otherwise pulling the capture thread 132 from the feed vessel 122 and through the catheter shaft 104. The motor can be powered either manually by the patient or electrically by the battery 107 and/or another type of energy source such as solar, thermal, radiant, chemical, electrical, motion, sound, elastic or gravitational energy. The motor can drive the thread 132 linearly, rotationally, helically, and/or along other predetermined path through the catheter shaft 104 using various techniques including but not limited to a conveyer belt or a cork-screw mechanism extending through the one or more lumens of the catheter shaft 104. In one embodiment, upon initiation of the rotational motor, the capture thread 132 migrates into the lumen 140 (see, for example, FIG. 4) of the catheter shaft 104, whereby it can communicate with the blood, tissue, or other organic matter through the ports 143 extending through the wall of the catheter shaft 104, for example, the side wall of the catheter shaft 104, to the catheter lumen, and returns into the collection vessel 124 (See FIG. 2A). In some embodiments, the rotation rate or other parameter of the capture thread 132 is adjustable, and altered based on parameters of the drive motor 106, the thread type, location of catheter placement in the body, and/or the patient's pathological condition. In some embodiments, a user can adjust or set the speed of the drive motor of the drive system 106 externally, and the motor can operate to alert the user and stop automatically when necessary, for example, by communicating with a hardware processor of the system when a malfunction is detected.

In some embodiments, the catheter shaft 104 accommodates the capture thread 132 for capturing harmful molecules in a patient's bloodstream to prevent a detrimental outcome in the body. The capture thread 132 is constructed and arranged in the catheter shaft 104 to rotate within the bloodstream distal to a check valve 134 (described herein) that functions as a seal to prevent bodily fluid of interest in the venous vessel from flowing to the proximal end of the catheter shaft 104 where the feed vessel 122 and collection vessel 124 are housed. As shown in FIG. 1, the capture thread includes a first portion 132A extending from the feed vessel 122 to a guide pin 137 at a distal end of the catheter shaft 104, and a second portion 132B extending from the first portion 132A about the guide pin 137 to the collection vessel 124. In some embodiments, the feed vessel 122 receives and secures a rotatable spindle or spool of the capture thread 132, which can be removed when the collection vessel 124 has received some, most, or all of the capture thread 132 whereby the feed vessel 122 is empty or nearly devoid of capture thread 132. Here, the spindle or spool can be replaced with a new spool of capture thread 132 which can be inserted into the feed vessel 122 and an end of which can be threaded into the catheter to allow the thread 132 to be inserted through the shaft 104 to the collection vessel 124. Similarly, the capture thread 132 spooled at the collection vessel 124 can be removed and replaced with the new source of thread from the new spool or spindle of thread 132. In other embodiments, the capture thread 132 is not removable from the collection vessel 124 and/or feed vessel 132 so that the entire apparatus 10 is disposed of after the capture thread 132 performs a single rotation from feed vessel 122 to the collection vessel 124 during which it passes through a source of blood, tissue, or other organic matter or a liquid solution including analytes or molecules of interest.

The rotational feature of the capture thread 132 offers several advantages. There is an unlimited supply of capture thread 132 spooling from the feed vessel 122. In some embodiments, the feed vessel 122 can be replenished with new spools of capture thread 132 as needed. Another advantage is that there are no fouling issues with the rotating capture thread, as fresh thread is continuously fed into the catheter shaft, and old thread is collected in the collection vessel 124. Also, the rotating thread 132 does not saturate with the analyte, as fresh thread continuously feeds into the system, i.e., originating at the feed vessel 124 and rotating through the catheter shaft 104 until the thread 132 terminates at the collection vessel 124.

The rotatable capture thread 132 is enclosed in the catheter shaft 104 of the endovascular probe for use in various applications including but not limited to analyte capture, endovascular oxygenation, and diagnostic analysis, each described in greater detail below. In doing so, the capture thread 132 can be shielded by the catheter shaft 104 or be freely accessible in the patient's vasculature system or the like.

In embodiments, where the capture thread 132 is rotatable about its longitudinal axis when positioned in the feed vessel 122, the catheter core, or lumen, can include a track, groove, or other mechanical pathway (not shown) for movement of the capture thread 132. Here, the capture thread 132 has a grip that locks into the core track, such that even if the catheter is bent, the capture thread 132 remains centered at the core of its lumen. In some embodiments, as shown and described with respect to FIG. 13E, the indentations or the like of a capture thread 132E can provide a grip lock feature, to grip the track during rotation, in addition to other features described below.

The rotatable capture thread 132 can be molded, machined, or otherwise formed of non-porous or porous materials identified in examples herein, in single lumen or multilumen configurations, hollow or solid configurations, and/or as indented configurations, for example, shown and described with respect to FIGS. 13A-13H. In particular, FIG. 13A illustrates a non-porous thread 132A. FIG. 13B illustrates a porous thread 132B. FIG. 13C illustrates a dual-lumen thread 132C. FIG. 13D illustrates a multi-lumen (more than two lumen) thread 132D. FIG. 13E illustrates an indented thread 132E. FIG. 13F illustrates a hollow thread 132F. FIG. 13G illustrates a porous hollow thread 132G. FIG. 13H illustrates a porous hollow thread with walls 13H. In some embodiments, a static catheter shown and described in FIGS. 9A-9D may include a thread 132A-132H (generally, 132). Such materials forming a foregoing capture thread 132A-132H may include a non-absorbable medical grade material such as PTFE, ePTFE Polypropylene, Nylon, Silicone, Polyester, PVDF, silk, or stainless steel threads. Other materials may include but not be limited to Acrylonitrile Butadiene Styrene (ABS), Acetal, Arnitel, Bionate, Carbothane, Chronosil, EFEP, Elastollan, ETFE, EVA, EVAL, ePTFE, FEP, HDPE, Hytrel, Kynar PVDF, LDPE, LLDPE, Medalist, NEOFLON™ EFEP RP-5000, NEOFLON™ PFA AP-210, Nylon 11, Nylon 12, Nylon 6, Pebax 35D, Pebax 45D, Pebax 55D, Pebax 63D, Pebax 70D, Pebax 72D, Pebax/EverGlide, Pebax/Mobilize, Pebax/PEBASlide, Pebax/ProPell STM PEEK, Pellethane 55D, Pellethane 75D, PET, PFA, Polycarbonate, Polypropylene, Polysulfone, Polyethersulfone, Polystyrene, Primacor, PVC, PTFE, Resin, Rezilient, Santoprene, SEBS, Silk, Tecoplast, Tecothane, Texin, and Thermoplastic Polyimide, or the like.

Referring again to FIG. 13E, an indented capture thread 132E can be used for applications that includes holes, indentations, or the like for the capture of cell components. The indentations provide regions for binding cells, and preventing detachment of captured cells at the check valve 134. In particular, a capture thread during rotation may contact the check valve 134 causing captured cells to be inadvertently removed from the thread. The indentations or the like in the capture thread 132E prevents cells from being separated because they are instead positioned in the indentations and therefore cannot be removed at the check valve 134.

Figure 19A:
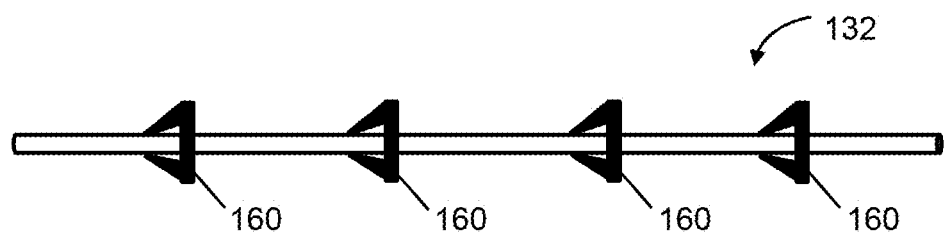
FIGS. 19A and 19B are illustrative views of an endovascular thread with cell scrapers, in accordance with some embodiments.
Figure 19B:
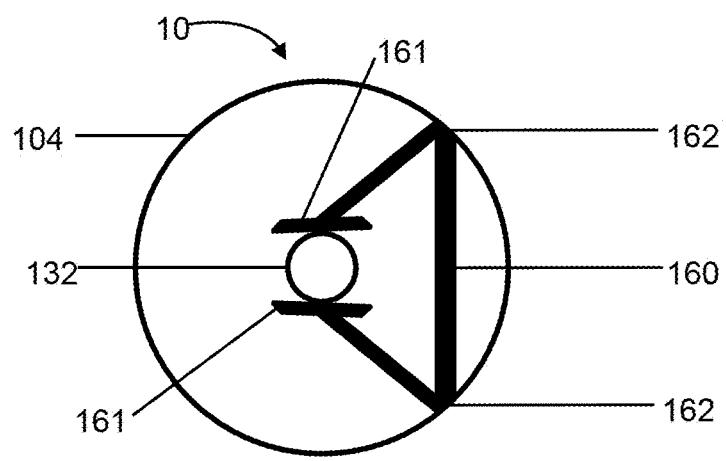

As mentioned above, the endovascular apparatus may be used for the collection of cells and other components. Referring to FIGS. 19A and 19B, the endovascular apparatus may further comprise at least one cell scraper 160. The at least one cell scraper 160 comprising a scraping element 161 such as a sharp pointed edge and at least one attachment element 162 configured to attach to the catheter 104. The scraping element 161 may be a straight edge, curved edge, or combination thereof and at least partially surrounds the circumference of the rotating thread 132. The cell scraper 160 allows the endovascular apparatus 10 to function as a cell collection apparatus. Thus, the endovascular apparatus 10 could be used as a method of apheresis, including plasmapheresis, thrombapheresis, and leukapheresis; for lectin-based broad-spectrum capture of viral hemorrhagic fever (VHF) viruses; or for extraction of cellular components from animals such as fetal bovine serum. Use of cell-scrapers in the catheter may allow for unlimited capture of the desired cell without the risk of cells binding to the thread.

In one embodiment, the rotational system is used as a method of plasmapheresis. The capture thread is coated with a hydrophobic and charge-based coating for non-specific capture of serum proteins and molecules. The hydrophobic and charge-based material may be embedded in size exclusion material to selectively capture desired blood components based on their size, and to exclude essential blood components. In some embodiments, the catheter comprises at least one cell scraper which eliminates the risk of cell binding, and allows for long-term capture of plasma proteins and molecules. The described plasmapheresis approach can be used in humans, animals, and as a general protein or molecule extraction technique. A key application in humans is for use as an anti-aging strategy through plasma dilution. Plasma dilution by removal of old harmful plasma proteins and molecules can be used to reverse signs of aging. Furthermore, such plasmapheresis strategy can be used to selectively remove blood components for treatment of complications such as sepsis, cytokine storms, crush injury, end-stage renal disease, and others. When used for non-human application such as for extraction of FBS, the animals can remain alive after extraction.

In other examples, for example, shown in FIG. 13A, a smooth or indented capture thread surface can be used for capture and oxygenation applications based on the size of the capture moieties and the captured cargo. In other examples, for example, shown FIGS. 13F-13H, a hollow capture thread configuration can be used to capture plasma and waste products. In other examples, a single lumen side portal is present at the very proximal end of the catheter for drug delivery or blood sampling applications.

As described above, another feature of the indented capture thread 132E is to interact with the movement mechanism with teeth, such as those of a conveyor track in the catheter shaft 104 and/or enclosure 102 or other protrusions for enhanced gripping of the capture thread 132E. The movement mechanism interacting with the rotating core track can assist with the movement of the capture thread 132. The capture thread movement system (not shown) can be configured to prevent any kinking or sticking of the capture thread 132 inside the catheter shaft 104 throughout. In some embodiments, the capture thread rotation rate is adjustable with increase or decrease buttons on the endovascular apparatus 10 or controlled wirelessly, which can control the drive system 106 which in turn operates the mechanical elements that rotate the capture thread 132.

In some embodiments, the capture thread 132 is a hollow capture thread coated with an ultrafiltration membrane or the like and placed under vacuum pressure to draw out a source of dialysate for performing an endovascular hemodialysis procedure for treating diseases such as end-stage kidney disease. An ultrafiltration material used to coat the thread 132 may comprise a polysulfone material with pore sizes ranging less than 0.04 um or greater than 0.7 but preferably 0.03-0.7 μm. However, in other embodiments, alternative materials may include, but not limited to, cellulose diacetate, cellulose acetate, nitrocellulose, cellulose esters, polysulfone (PS), polyethersulfone, polyacrylonitrile, polyaminde, polyimide, polyethylene, polytetrafluoroethylene, polyvinylidene fluoride, polypropylene, polymethylmethacrylate. In some embodiments, the hollow capture thread 132 can have occlusions every few centimeters to act as check valves to contain and move the captured plasma as the thread rotates in the catheter. This rotating hollow fiber capture thread may be used for endovascular plasmapheresis to remove plasma for treatment of diseases including paraproteinemia, hyper viscosity syndrome, rhabdomyolysis, kidney failure, and range of autoimmune diseases, as well for removal of plasma from animal sources including cruelty-free extraction of fetal bovine serum instead of the current inhuman method of a fetal blood harvest. Other rotating non-hollow capture threads, for example, shown in FIGS. 9A-1 and 9A-2, may be used for therapeutic apheresis or hemodialysis applications.

Another feature is that the continuous rotation of the capture thread 132 prevents fouling of the membrane. Fouling may refer to the accumulation of undesirable materials such as protein, lipids, nucleic acids, cells, and microorganisms. The rotating endovascular apparatus 10 does not suffer from fouling as fresh thread 132 is continuously fed into the catheter via the feed vessel 122 and old thread, even if fouled, is removed and collected in the collection vessel 124.

In some embodiments, the capture thread 132 is functionalized using ammonia plasma treatment, SATA/SMCC, click coupling, and various other conjugation chemistries, for coating with capture moieties. In other embodiments, the capture thread 132 is functionalized using cross-linked trimethoxysilane. In such embodiments, silicone rods are treated with oxygen or air plasma and then functionalized using amino-silanization with crosslinkers such as N-(2-aminoethyl)-3-aminopropyltrimethoxysilane (APTMS). The silicone rods are then modified with bifunctional PEG linkers including maleimide-PEG-NHS Ester. Capture moieties include chemicals, peptides, antibodies, proteins, nucleic acids, porous microspheres, affinity microspheres, nanoparticles, or other materials for capture or delivery of molecules. Examples of specific capture moieties include zirconium phosphate for hyperammonemia, deferoxamine isothiocyanate for hemochromatosis, antigens and moieties for autoantibodies, staphylococcal protein A and peptides for immunoglobulins, antibodies for cytokines, antibodies for LDL and other lipoproteins, antibodies for cell surface determinants, chelators for metals, porous microspheres for small molecules and small proteins, perfluorocarbon nanoparticles and hemoglobin-based nano- and microparticles (e.g. polybag-SOD-Catalase or PolyHb-Catalase-SOD-Carbonic anhydrase for oxygenation and carbon dioxide capture), magnetic moieties for capturing magnetic particles, capture moieties for clotting factors, as well as for pathogens, and range of non-cellular and cellular components.

In some embodiments, sorbent polymeric porous beads of varying pore sizes and bead sizes are used in the capture thread for capture of a range of molecules. These sorbent materials include poly-styrene, poly(styrene-divinylbenzene), crosslinked composite dextran matrix, agarose-dextran, silica gels, and other sorbent porous beads. Porous beads provide a wide-range of uniform pore sizes that will be used for capture of desired range of undesirable molecules, from small molecules to proteins. In other embodiments, superabsorbent materials are used in the capture thread 132, e.g., in the core, in the matrix, or on the surface of the thread 132, for purposes of water removal can include, acrylic acid, acrylamide and polyvinyl alcohol (PVA), N,N-dimethylacrylamide (DMAA), carboxymethyl cellulose-PEG, Soy protein/poly(acrylic acid), Polyacrylate/polyacrylamide, organic montmorillonite (OMMT)/poly(acrylic acid), sucrose and other carbohydrate-based hydrogels. Superabsorbent hydrogels have been developed that have very high water absorbing properties. N,N-dimethylacrylamide (DMAA) have a swelling ratio of about 3000 but not limited thereto, where they can absorb 3000 times their weight in water. Superabsorbent crosslinked carboxymethyl cellulose-PEG hydrogels have swelling degrees of up to 5000%.

In some embodiments, as previously described, the check valve 134 prevents the flow of blood to the outside of the body, and any liquid in the feed and collection vessels from entering the blood, and further prevents the leakage of fluids into or out of the vasculature. The check valve 134 may be incorporated in the proximal end of the catheter, and formed of an elastic liquid silicone polymer, for example, a durometer silicone component in the catheter 104, to create a narrowing or seal to prevent flow of liquid. In some embodiments, an elastic liquid silicone polymer is provided in the catheter to create a narrowing or seal to prevent flow of liquid, which is beneficial in certain applications, for example, where the catheter shaft 104 operates as a filtration device. If the capture thread 132 is drawn into a narrowing of smaller size, then that narrow tubing can act as a check valve. The narrow tubing check valve would prevent flow of blood to the outside of the body, and any liquid in the feed and collection vessels 122, 124, i.e., saline as described herein, from entering the blood and/or prevent gases such as air from entering the vessels 122, 124 due to the presence of the fluid occupying the vessels 122, 124.

Figure 6:
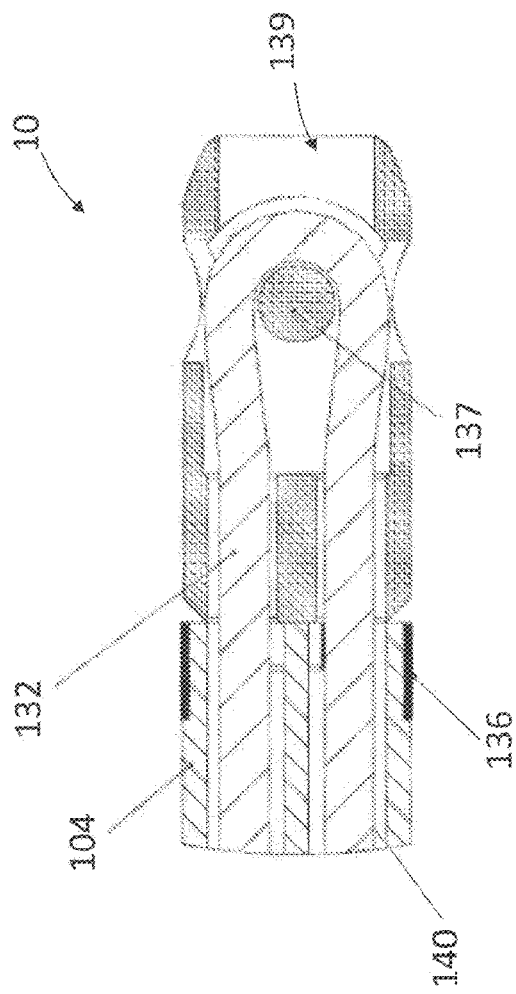
FIG. 6 is an enlarged cross-sectional side view of the distal end of the wearable endovascular apparatus of FIG. 1.
Figure 4:
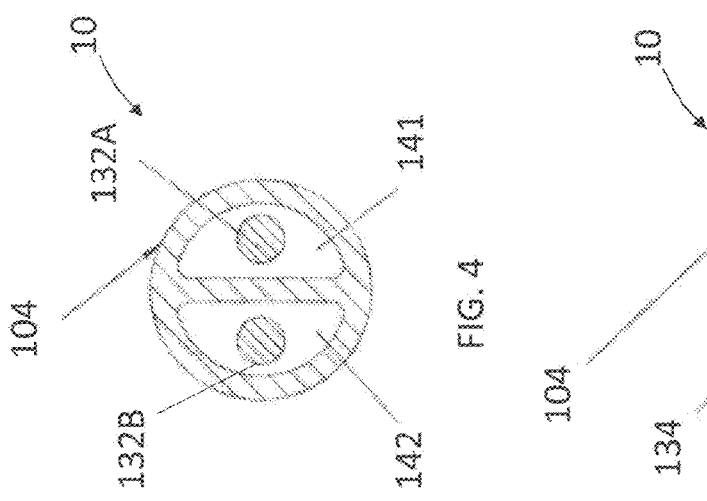
FIG. 4 is another cross-sectional view of the wearable endovascular apparatus of FIG. 1.
Figure 5:
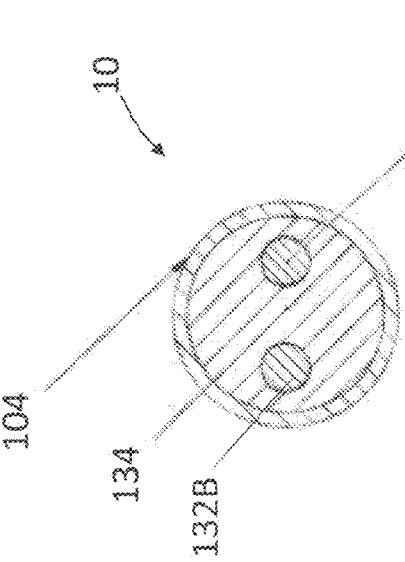
FIG. 5 is another cross-sectional view of the wearable endovascular apparatus of FIG. 1.

In some embodiments, the distal end 108 of the catheter shaft 104 includes a longitudinal opening 139 to allow the entry of blood or other fluid into the general catheter lumen 140, shown in FIG. 6, or in particular, the incoming lumen 141 shown in FIG. 4. The opening 139 may be the only opening to the capture thread 132, or may be in lieu of, or in addition to a plurality of ports 143, described below. In some embodiments, the catheter tip 108 includes a radiopaque marker 136, for example, formed of tungsten and/or other radiopaque material for aiding in catheter placement in a patient using fluoroscopy or other radiation-based medical technology. The tip 108 is constructed and arranged to capture the bodily fluid or aid in a specified treatment. A tip guide 137 at the tip 108 may be a stainless steel pin or the like about which the thread 132 rotates to reverse course. In other words, a position at which the thread changes direction of motion from a distal direction to a proximal direction.

In some embodiments, the thread 132 extends from a proximal position to a distal position of the catheter and returns from the distal position back to the proximal position. In such embodiments the proximal and distal positions can be located at or near the proximal and distal ends of the catheter or can be located at body positions of the catheter that are located at body positions of the catheter spaced apart from the actual ends of the catheter. The terms "proximal end", "distal end", "proximal position", and "distal position", as used herein define positions of the catheter both at or near the ends of the catheter and at body positions of the catheter spaced apart from the actual ends.

The catheter shaft 104 provides a structure for the capture thread 132 to rotate within the bloodstream distal to the check valve 134. In doing so, the catheter shaft 104 also provides protection of the venous vessel in which the catheter shaft 104 is inserted, so that a lumen wall of the venous vessel does not directly contact the circulating thread 132 rotating inside the catheter shaft 104 but also having openings or ports 143 which allow blood to contact the capture thread 132. The catheter shaft 104 may have one or more lumens extending through the length of the shaft 104 for the capture thread 132. As shown in FIG. 4, in the case of a dual lumen catheter shaft, i.e., including an incoming lumen 141 and a return lumen 142, one lumen 141 may function as the incoming pathway for the capture thread while the other lumen 142 functions as the return pathway to prevent the capture thread 132 from tangling. The lumens 141, 142 of the catheter shaft 104 may be circular, semi-circular, ovular, crescent, or polygon shaped depending on what is required to match or otherwise accommodate the shape of the capture thread 132 and allow clearance while also permitting blood to flow through the shaft 104 and contact the capture thread 132. In some embodiments, the catheter shaft 104 further includes lumens for additional structural or anchoring members or access for tools and the like.

The catheter shaft 104 may include additional lumens extending therethrough which can be used for dispense/aspiration ports 143, which open the catheter shaft 104 to blood flow through openings in the shaft material forming the body of the shaft 104, or used as guide wire lumens, lumens for additional structural or anchoring members or access for tools. The ports 143, also referred to as openings, may be circular, ovular or elliptical holes which are drilled, laser cut, water-jet cut, die punched, molded, skived, or formed by well-known processes. If the ports 143 are discrete they may be spaced 0.5 to 100 mm apart, but not limited thereto, in order to optimize blood flow. The ports 143 may be oriented perpendicular or parallel to the septum that separates the inner lumens, or angled between the two. They may be regular or irregular patterns oriented in one or multiple axial lines down the catheter shaft 104, or in a helical or random around the catheter shaft main axis. Alternatively, the ports 143 may also be created during the extrusion process by creating an open pathway as part of the circumference of the extrusion which will allow blood to flow in and out of the catheter shaft distal to the check valve 134. Increasing the number and dimensions of the ports 143 can decrease the tensile, compressive and torsional strength of the catheter shaft 104, which will increase likelihood of the catheter kinking from the forces exerted on it by the circulating capture thread. Additionally, the ports 143 may not be symmetric about the catheter shaft axis, which can cause the strength of the shaft 104 to be non-uniform making kinking in certain orientations more likely and also impacting insertion properties of the catheter such as pushability and torquability, or related forces.

Figure 2A:
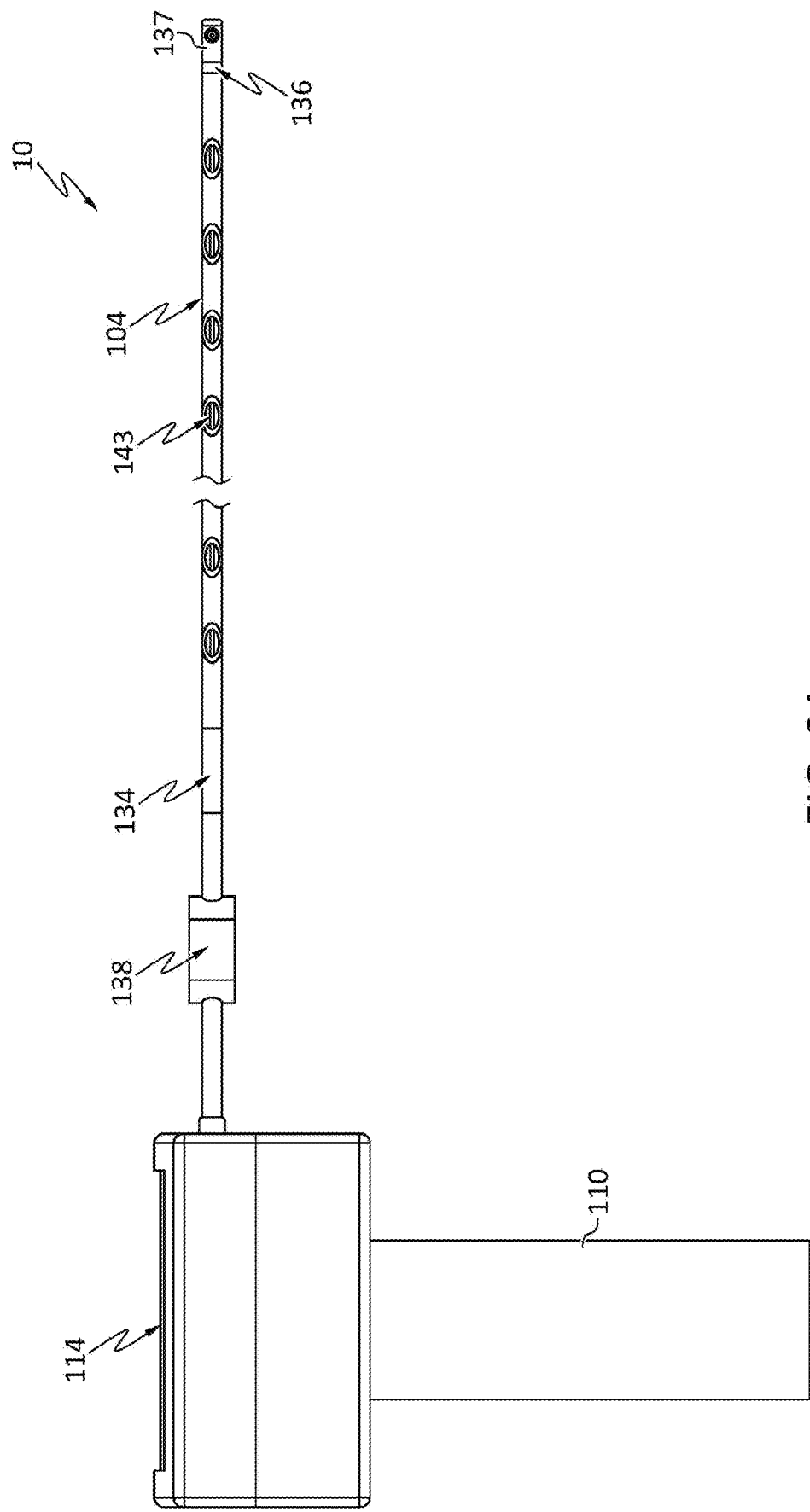
FIG. 2A is a top view of the wearable endovascular apparatus of FIG. 1 in accordance with a first embodiment.
Figure 2B:
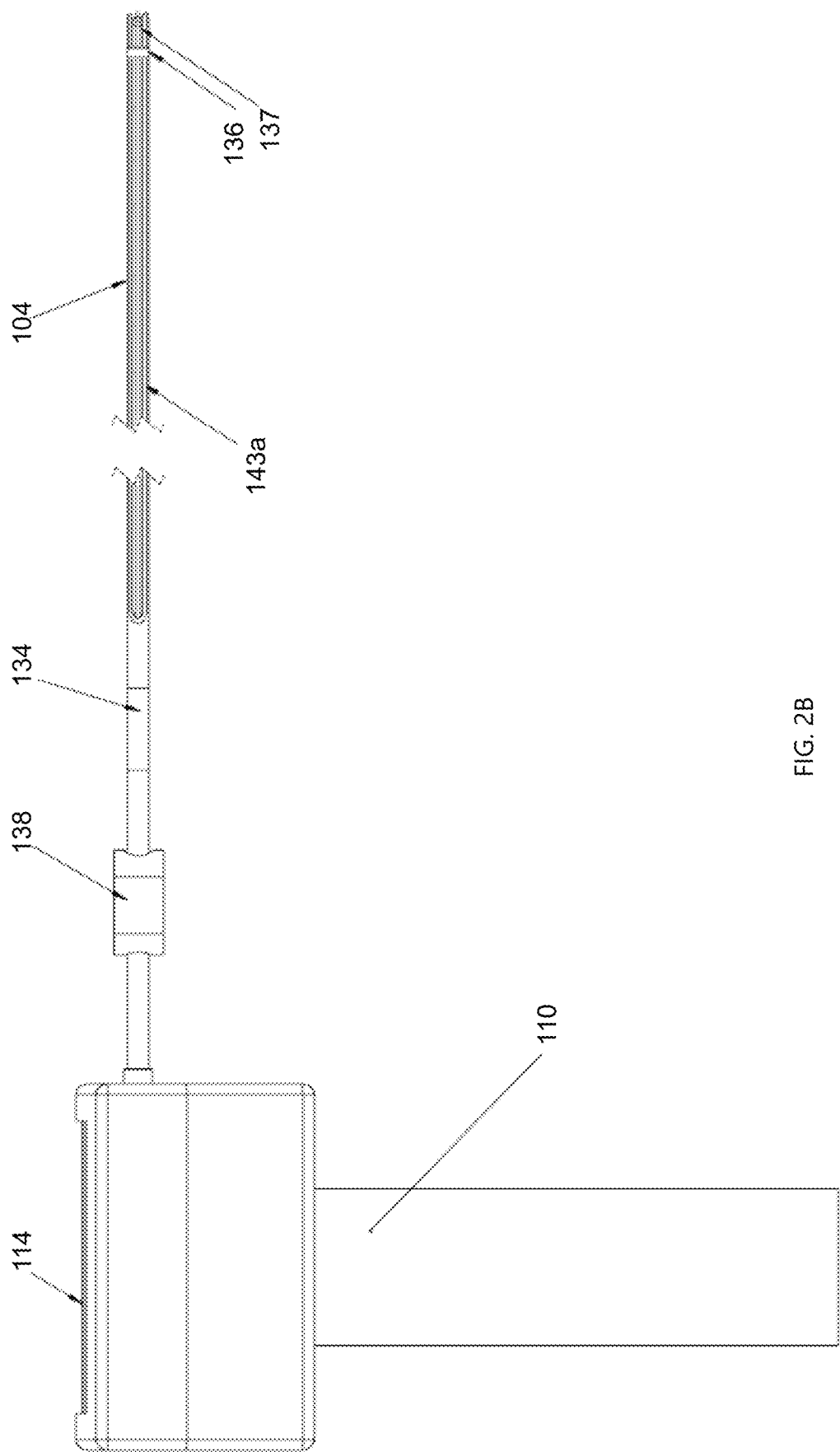

While the catheter 104 may comprise a plurality of ports 143 as exemplified in FIG. 2A, the present invention may contain other embodiments as shown in FIGS. 2B-2E. Referring now to FIGS. 2B and 2E, the present invention may comprise at least one port 143a extending along the shaft of the catheter 104 so that the top and bottom regions of one end of the catheter 104 are exposed. As shown in FIG. 2E, the ports 143a are located along both the top and bottom of the shaft of the catheter 104 and are elongated along a majority of the length of the shaft. Alternatively, the present invention may comprise at least one port 143b similar to the port 143a, except that port 143b does not expose the end region of the catheter 104 (See FIG. 2C) or exposes the entire end region of the catheter 104 (See FIG. 2D). The variation on port designs may be beneficial by allowing the capture thread 132 to have better access to blood or other bodily fluid.

In some embodiments, a feed vessel 122 and collection vessel 124 are housed in a sealed vessel enclosure 112, which in turn is in the wearable enclosure 102. In some embodiments, the sealed vessel enclosure 112 can be formed as a compartment or other region of the interior of the wearable enclosure 102 so as to be integral with the wearable enclosure 102. Alternatively, the sealed vessel enclosure 112 can be formed separately and inserted into and coupled with the interior of the wearable enclosure 112. Also included in the wearable enclosure 102 may include some or all of the drive system 106, a battery 107, and/or other mechanical, electrical, and/or electro-mechanical components required for operating the wearable endovascular apparatus 10. The sealed vessel enclosure 112 can prevent liquid in the feed vessel 122 and/or collection vessel 124 from escaping into the user's blood stream during insertion of the catheter 104. Since the feed vessel 122 and collection vessel 124 are immersed in liquid such as saline, air or other gases or liquids are not permitted from entering the vessel. The vessels 122, 124 must be immersed in liquid to ensure there is no chance of air getting to the circulation. The check valve 134 in intended to prevent leakage of fluids, but this feature provides an additional level of safety with respect to preventing air from accessing the vessels in the event that the check valve 134 fails.

In other embodiments, the feed vessel 122 and/or collection vessel 124 are external to the apparatus 10, in particular, the enclosure 102, so there is no sealed vessel enclosure 112. Regardless of location of the vessels 124, the catheter core can be divided into two half-cores, or lumens: one for entry into the collection vessel 124 and one for exit from the feed vessel 122. The half-cores or lumens of the catheter core may correspond to lumens 141, 142 shown in FIG. 4.

The feed vessel 122 functions to feed the capture thread 132 into the catheter 104. The feed vessel 122 can be removed from the device to troubleshoot or replace the thread 132 by the user or manufacturer or both. There can be one or more feed vessels 122 within the device such that the threads 132 can be running side by side and detecting multiple biomarkers or performing different functions, such as capturing water, removing molecules, and processing blood, which may include but not limited to filtering (capturing unwanted components), purifying, or the like. The dimensions of the feed vessel 122 could vary based on the type of the device, procedure, thread size, patient size, and other variables that help dictate the treatment of the patient. Multiple sensors and smart features can be integrated into the feed vessel 122 such that there is automatic detection of the thread type, constant tension control, speed identification and control, problems with the feed, and thread level. Sensors for detecting tension, weight, optics, and so on may provide these smart features. In some embodiments, the endovascular apparatus 10 includes one or more onboard or external sensors, such as but not limited to oxygen sensors, RBC sensors, and pressure sensors that communicate with processing hardware and software, which in turn can be onboard or external to the device such that a user, e.g., a patient, caregiver, or healthcare professional, can monitor real time diagnostics. In some embodiments, a weight sensor can determine a type of thread(s), thread features, number of threads, and how much thread is available. In some embodiments, an optical sensor determines a thread type, problems with the feed, and thread level. In some embodiments, a sensor measures the tension could monitor the thread level and any problems with the feed. Information collected from one or more of these sensors and smart features can be displayed on the device display 114 or transmitted to an external device to ensure the device 10 is functioning properly.

The collection vessel 124 collects the thread 132 once it has moved through the catheter, and typically after it has been in communication with a source of blood, tissue, or the like. The number of collection vessels 124 will be based on the number of threads and the amount of thread required for the particular treatment. For example, if the treatment required large volumes of thread, two collection vessels 124 can be placed in the device such that each vessel 124 could collect a portion, for example half, of the thread. Alternatively, in embodiments including multiple thread types, one collection vessel 124 collects all of the threads or multiple collection vessels 124 can be placed in the device such that each thread has a separate collection vessel. The ability to have multiple collection vessels 124 enables the threads 132 to be set at independent speeds based on the treatments required. The collection vessel 124 can be removed such that a user or manufacturing or both can access the collection vessel 124. The collection vessel 124 could feed into a diagnostic or treatment analyzer that is onboard the device or external to the device. Smart features can be integrated into the collection vessel(s) 124 to let the user know when the vessel is full, speed, stopped, type of vessel, or when there is a problem with the vessel or device. The collection vessel 124 can be motorized by attaching a gear, wheel, or related mechanical element to a motor that rotates the collection vessel 124, which in turn winds the thread 132 or threads onto a collection vessel 124. In some embodiments, there can be multiple motors driving multiple vessels, or one motor capable of driving multiple vessels simultaneously, for example, the feed vessel 122 as well as the collection vessel 124. Various mechanisms can be used to wind the vessel including but not limited to gears, belts, and magnets. The collection vessel 124 can be unique to the treatment or universal allowing it to collect any embodiment of the thread 132. The vessel information, both function and physical properties, can be collected and reported out to the device display.

In some embodiments, the electronic display 114 is coupled to or integrated with a sidewall of the enclosure 102 at the proximal end of the wearable endovascular apparatus 10. In various embodiments, the display 114 could be attached to the device or could be external to the device. If external, the device could read out to the display wirelessly or by a cable. The display 114 may be powered by the battery 107 in the enclosure 102. The display 114 may receive and display vessel information, both function and physical properties, collected and reported out to the device display via the collection vessel 124 at the probe tip 108 and/or capture thread 132. The display 114 may provide a user the ability to control various elements of the endovascular apparatus 10, including but not limited to speed control, stop, start, replace the thread or troubleshoot the apparatus 10. The endovascular apparatus 10 may include buttons, a touchscreen or other mechanisms by which the user can interact with the display and device. For safety, the endovascular apparatus 10 my display a warning if there is a kink in the catheter 104, oxygen bubble in the line, thread misalignment, an RBC leakage, or other malfunction of the apparatus 10. A warning could be in the form of an audio, haptic, and visual alarm. The alarms and data collected by the endovascular apparatus 10 could also be read out to the electronic medical record, caregiver, of physician wirelessly or through a connection to a device. The endovascular apparatus 10 could be charged by induction, plug, solar or batteries and the display 114 could show the charge level and alarm as the battery 107 needs to be charged or replaced. The software and display interface could allow the user to load and remove the capture thread 132 from the device easily, without supervision from a healthcare professional.

Figure 11:
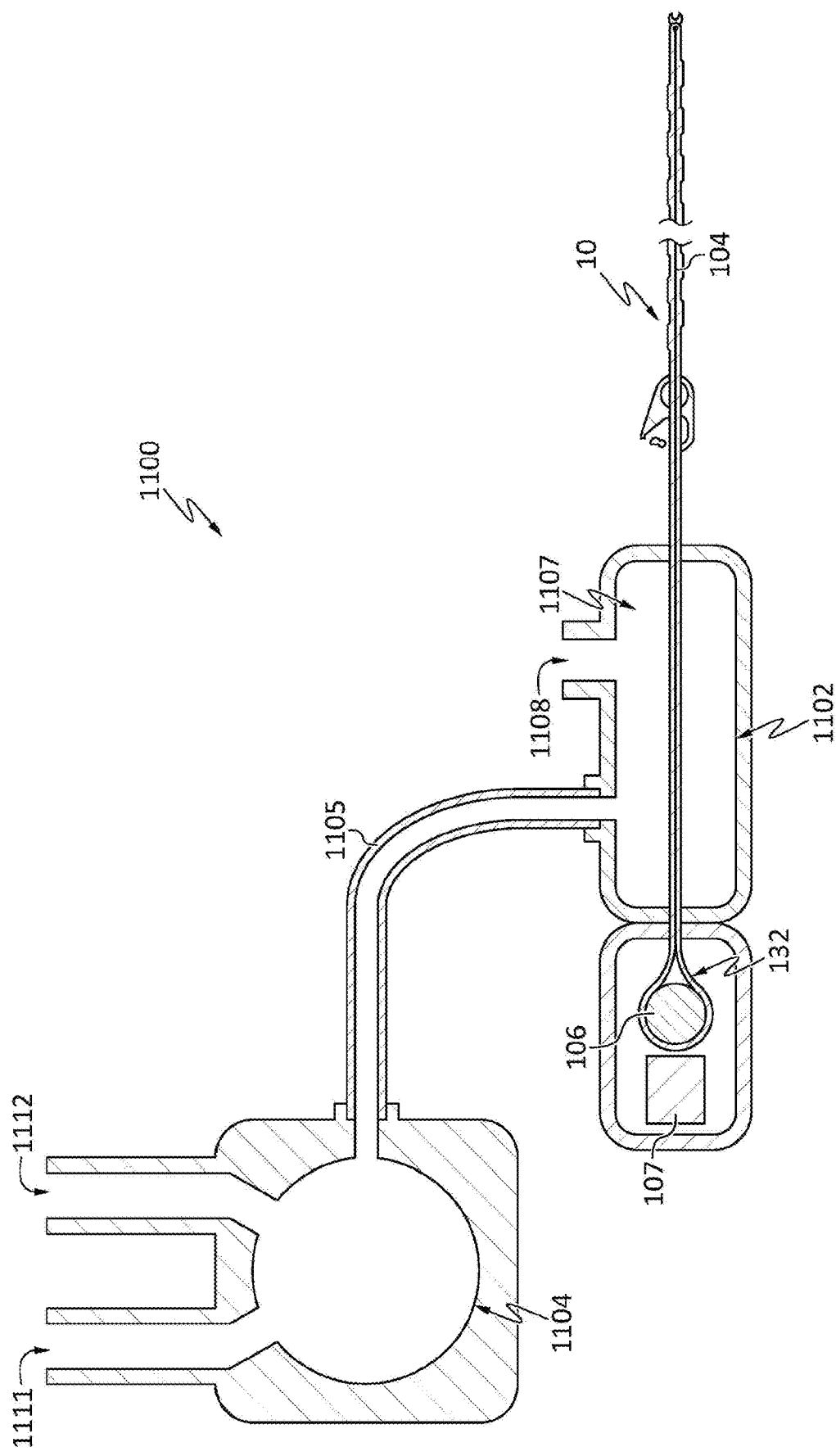
FIG. 11 is a cutaway side view of an endovascular oxygenation system, in accordance with some embodiments.

In some embodiments, the endovascular apparatus 10 can be part of an endovascular oxygenation system 1100, for example, shown in FIG. 11, which provides oxygen to the patient on a predetermined and unlimited basis, for example, supplying oxygen for minutes up to multiple days, weeks, or years. Similar to the configuration shown in FIG. 1, the thread 132 can rotate, translate, and/or otherwise transfer from the feed vessel 122 through the endovascular catheter shaft 104 to the collection vessel 124 during which the system 1100 provides oxygen and removing $CO_2$ as the thread 132 rotates in the catheter 104. Herein, the system 1100 can provide an unlimited $O_2$ supply or at least a substantially greater $O_2$ supply that the abovementioned approaches, especially for long term usage. In other embodiments, the capture thread 132 is oxygenated, e.g., coated with an oxygenated hemoglobin and carbonic anhydrase and/or another coating that can aide in the removal of $CO_2$ or provide oxygenation or both. In some embodiments, an oxygenation thread 132 can be coated with oxygenating proteins or polymers, antioxidant proteins or small molecules, and $CO_2$ removing enzymes such as carbonic anhydrase, or $CO_2$ capturing moieties, such as small molecules, proteins, and polymeric beads, as shown in FIG. 12. The thread 132 can be conjugated with the oxygenated hemoglobin or perfluorocarbon-based polymers, along with antioxidant enzymes such as superoxide dismutase, catalase, or small molecules, and carbonic anhydrase for conversion of carbon dioxide to carbonic acid and bicarbonate ions. Various other nanoparticle-based oxygen delivery and $CO_2$ removal nanoparticles can also be utilized.

There are a range of perfluorocarbon and nano/microparticle-based oxygen carriers that will can be utilized for coating the thread 132. Perfluorocarbon-based oxygen carriers (PFCs) can include, but are not limited to perfluoro-n-octaine, perfluorodecalin, perfluorotributylamine, perfluorohexane, perfluorohydrophenanthrene, perfluorooctylbromide, octafluoropropane, perfluorodecane, perfluorodichlorooctane, perfluorotrimethylcyclohexane, perfluorotripropylamine, perfluorodimethyladamantane, perfluoromethyldecaline, perfluoromethyladamantane, perfluorofluorene, alumina-treated perfluorooctane, hydrogen-rich monohydroperfluorooctane, and mixtures thereof. An example of polymer-based oxygen microparticle delivery system is the polymer hollow microparticles (PHM) consisting of poly(D,L-lactic-coglycolic) acid (shell material), perfluorooctyl bromide (nonsolvent), and Pluronic F-68 (self-emulsifying agent). The nanoporous shell enable loading and release of oxygen gas by passive diffusion.

As shown in FIG. 11, the capture thread 132 extends through an oxygenator 1102, which communicates via a connector 1105 with a blender 1104. The blender 1104 includes a first inlet 1111 for receiving a source of air and a second inlet 1112 for receiving a source of oxygen, which are mixed together to provide a desired combination of oxygen and nitrogen, and more specifically, a desired concentration of oxygen for the oxygenator 1102.

The oxygenator 1102 includes a chamber 1107 that oxygenates the capture thread 132, but also removes $CO_2$ from the capture thread 132. The oxygenator 1102 includes an outlet 1108 for the removal of $CO_2$ and/or other undesirable elements from the thread 132. The blender 1104 provides a tuning mechanism that produces the desired fraction of delivered oxygen ($FDO_2$).

The capture threads 132 configured as diagnostic threads can be custom designed for detection of a range of analytes. Referring again to FIG. 12, designated sections 1202 of the diagnostic thread 132 can be coated with a single layer or plurality of layers of bioreceptors including antibodies, therapeutic proteins, enzymes, peptides, small molecules, and nucleic acids. The plurality of layers may be created using any standard means in the art including using genetically encodable linkers for enzyme mediated polymerization of proteins or using layered chemical conjugation of proteins. In some embodiments, these sections 1202, or regions, can operate as designated biomarker detection or analyte capture regions. The range of analytes to be measured include but not limited to sodium, potassium, chloride, ionized calcium, Urea Nitrogen (BUN)/Urea, Creatinine, glucose, lactate, TCO2, PCO2, sO2, pH, HCO3, base excess, anion gap, human chorionic gonadotropin, B-type natriuretic peptide, sCD40, copeptin, C-reactive protein, hemoglobin, hemoglobin A1c, IgG, IgA, IgM, IgD, IgE autoantibodies, Troponin C, Troponin I, Troponin T, creatine kinase, creatine kinase subunit M, creatine kinase subunit B, myoglobin, myosin light chain, lipase, amylase, fibrinogen, clotting proteins, von Willebrand factor, total cholesterol, LDL-C, HDL-C, triglycerides, vitamins, hormones, enzymes, small molecules, heavy metal ions, proteins, microRNA biomarkers, and circulating free DNA. The capture thread moieties can capture and detect metabolites and biomarkers and feed them into the apparatus 10 for real-time detection and management of the patient. For example, shown in FIG. 7, the endovascular apparatus 10 can interface with a biomarker analyzer 14 or the like. In this example, the capture thread 132 exits the catheter 104, which does not require the enclosure 102 or is configured so that the enclosure 102 can be detached from the catheter 104. Captured components transfer from the thread 132B to an external machine such as the analyzer 14. For example, the thread 132 is pulled by motors in the analyzer 14. Although not shown, the analyzer 14 in FIG. 7 can be positioned between portion of the thread 132B traveling in a direction of the collection vessel 134 and the collection vessel 134 itself. Depending on the rotation rate, for example, controlled by the drive system 106 alone or in concert with a computer or the like that controls the drive system 106, it can be used to determine precise metabolite and biomarker levels over minutes, hours, days, weeks, or other predetermined period of time.

Figure 14:
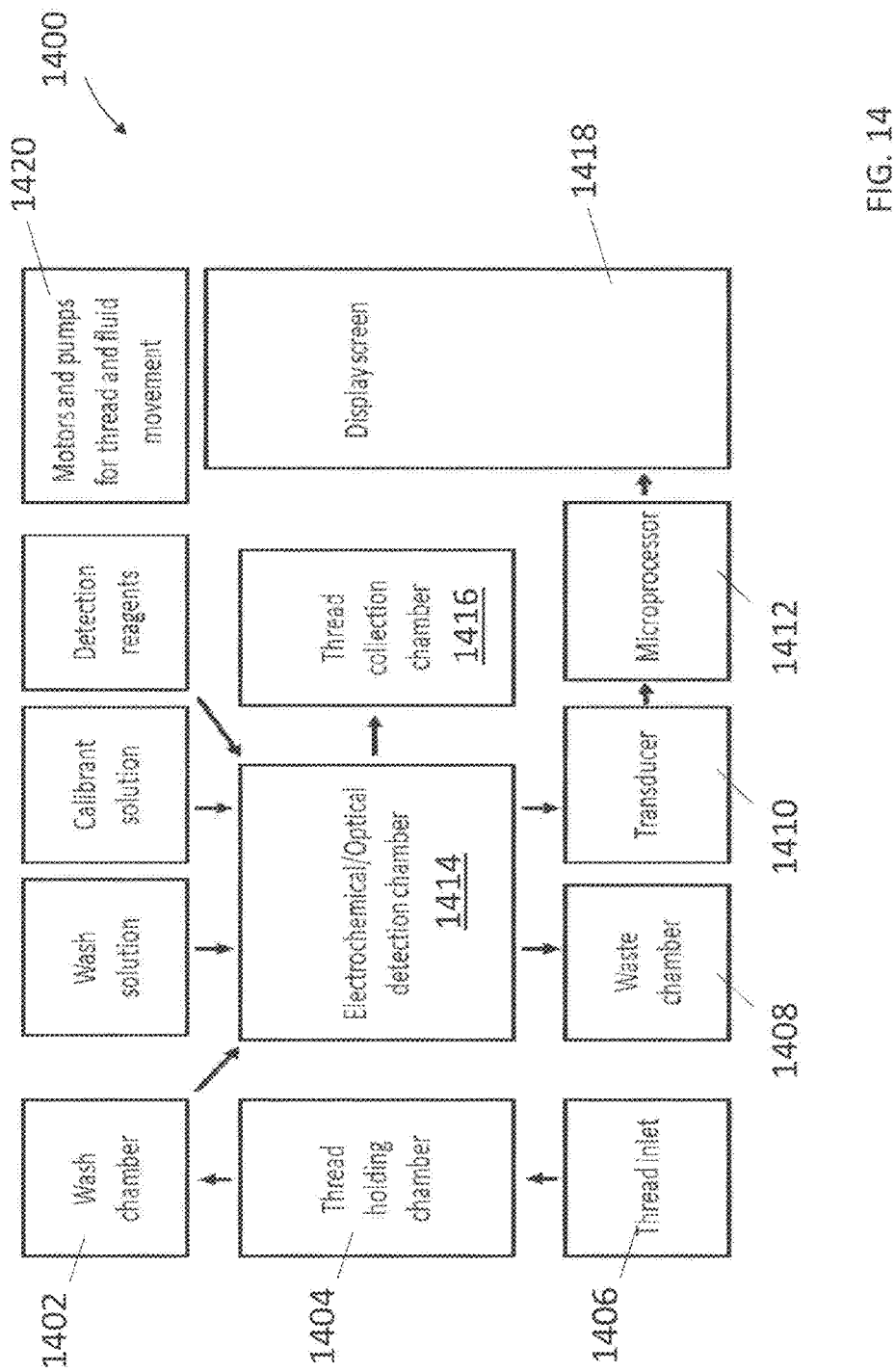
FIG. 14 is a block diagram of components of a point-of-care analyzer apparatus, in accordance with some embodiments.

FIG. 14 is a block diagram of components of a point-of-care diagnostic thread analyzer apparatus 1400, in accordance with some embodiments. The analyzer device 1400 can be used for both real-time and near real-time analysis of analytes captured by a capture thread 132 of the wearable endovascular apparatus 10 of FIGS. 1-13. The analyzer apparatus 1400 may include a wash chamber 1402, a thread holding chamber 1404, a thread inlet 1406, a waste chamber 1408, a transducer 1410, a microprocessor 1412, a detection chamber 1414, a thread collection chamber 1416, a display screen 1418, and a drive system 1420 including one or more motors, pumps, or the like for thread and fluid movement.

The apparatus 10 can analyze capture threads 132 constructed and arranged as long diagnostic threads, for example, threads incoming from a blood filtration probe or biological/non-biological sampling probe, and/or short diagnostic threads, e.g., in specialized cartridges designed for small volume samples. Biological samples to be analyzed include but not limited to blood, plasma, saliva, urine, cerebrospinal fluid, tissues, in vitro samples (cell cultures), pharmaceutical samples, food samples, and environmental samples.

The electrochemical and/or optical biosensors of the detection chamber 1414 perform a point-of-care analysis of the thread samples. Electrochemical of the sensor detection chamber 1414 can be potentiometric to measure difference in voltage, or amperometric to measure difference in current. The transducer 1410 conveys signals produced by the sensors 1414 for data analysis to the microprocessor 1412, which outputs the data to the display screen 1418. Optical biosensors of the electrochemical/optical detection chamber 1414 can include fluorescence, luminescence, transmission, and scattering biosensors. Electrochemical sensors of the detection chamber 1414 will include ion selective sensors for detection of sodium, potassium, chloride, ammonium, calcium, carbon dioxide, and the pH. Amperometric sensors of the detection chamber 1414 will be used for detection of molecules, such as glucose, lactate, creatinine, and oxygen. Immunosensors of the electrochemical/optical detection chamber 1414 can include both indirect labeled and direct non-labeled approaches. Immunosensor labels can include enzymes such as glucose oxidase and catalase for amperometric detection of oxygen, urease for potentiometric detection of ammonium, peroxidase for amperometric detection of hydrogen peroxide, and alkaline phosphatase for amperometric detection of aminophenol or phenol.

Electrochemical immunosensors or ligand/ligand receptor-based biosensors of the detection chamber 1414 will utilize antibodies or ligands for capture and detection of the target analyte. Antibodies immobilized on the thread surface or matrix upon binding to target analyte generate signal through production of electroactive species in the detection chamber. These can include for example addition of secondary antibody conjugated with enzyme such as alkaline phosphatase (ALP) and interaction with substrates such as p-aminophenol or phosphorylated ferrocene to generate changes in the voltage or the current.

Electrochemical sensors of the detection chamber 1414 can utilize different electrode design configurations. In one configuration shown in FIG. 15A, a cylindrical electrode 1514 surrounds the diagnostic thread 132 and separated by a gap. Walls 1504 separate each designated diagnostic thread region. Holes 1501 in the electrodes 1534 allow a flow of wash from the wash chamber 1402, which receives a source of a thread 132 from the thread holding chamber, and outputs the thread 132 to the detection chamber 1414, which can also receive detection reagents into each designated detection area.

Figure 15:
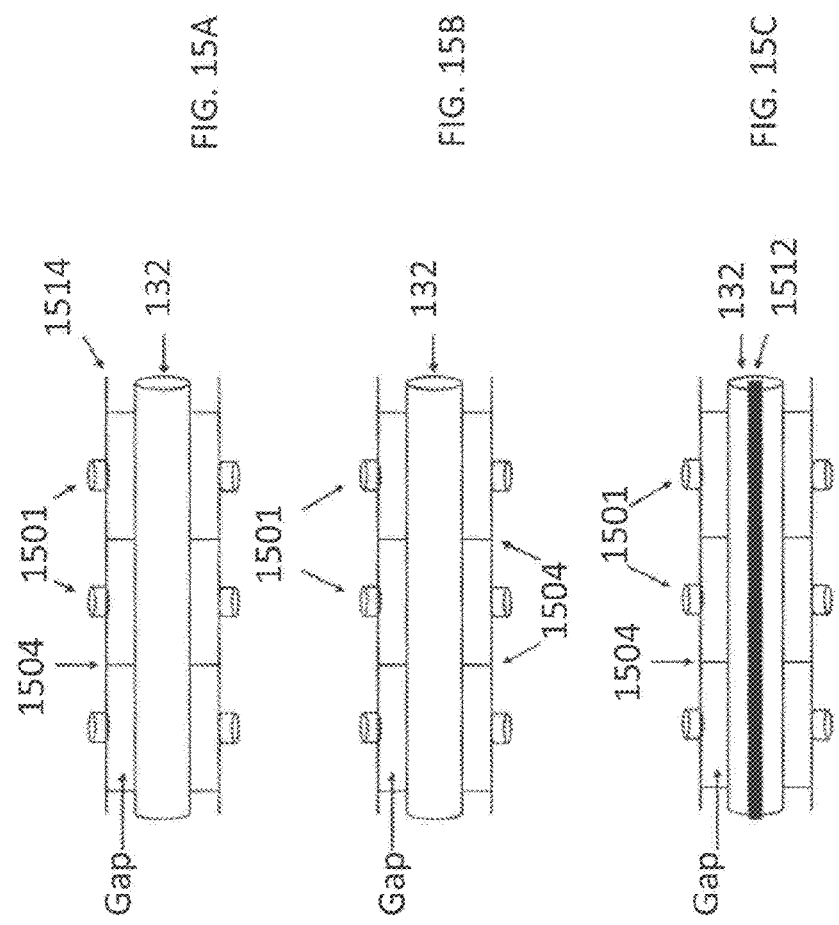
FIGS. 15A-15C are side views of various configurations of an electrochemical sensor of an endovascular apparatus, in accordance with some embodiments.

As shown in FIG. 15B, in some embodiments, the thread 132 enters a cylindrical chamber 1414, where the separation walls themselves act as the electrodes 1514. Holes 1501 in the cylindrical chamber 1414 allows a receipt of a combination of wash, calibrant, and detection regents into each designated area of the chamber 1414. All waste flows into the waste chamber 1408.

In another configuration, as shown in FIG. 15C, the electrode wire 1512 or electroactive matrix inside the core of the diagnostic thread 132 functions as an electrode 1512. Cylindrical chambers and walls 1504 provide separation in between the diagnostic regions. For all configurations walls with hydrophobic coatings to prevent flow in between the detection regions. Volumes pumped by a pump of the drive system 1420 (FIG. 14) can be from 1-200 microliters. The miniaturization reduces sample volume and the cost, while maintaining high sensitivity. The analyzed thread is collected in the thread collection chamber 1416.

As shown in FIGS. 9A-1 through FIG. 9D-2, a rapid endovascular capture probe is constructed and arranged as static capture thread probe 900A-900D (generally, 900) that allows for the rapid capture and removal of desired undesirable molecules and enzymatic detoxification of blood components for short-term acute disease applications where longer threads are not required. Another advantage of the static capture probe 900 is that it can be very narrow in size, as there are no rotating components such as a rotating capture thread, motor to drive the thread, and so on. Therefore, the probe 900 can be beneficial to neonatal, pediatric or other patients who have difficult to access veins. The static capture probe 900 can be used to display therapeutic enzymes for treatment of a range of pathological diseases, including metabolic diseases, and for metabolism of toxins. Therapeutic enzymes may be any mammalian or microbial-derive enzyme including but not be limited to creatinase, urease (detoxification of urea), uricase (detoxification of uric acid), carbonic anhydrase ($CO_2$ detoxification), thiosulfate cyanide transsulfurase (detoxification of cyanide), alcohol oxidase (alcohol detoxification), alcohol dehydrogenase (alcohol detoxification), glutamine synthetase (detoxification of ammonia), phosphodiestrase (detoxification of organophosphates), acetylcholinesterase (detoxification of organophosphates), paraoxonase 1 (detoxification of organophosphates), butyrylcholinestrase (detoxification of organophosphates), arginase (metabolism of arginine), L-asparaginase (depletion of asparagine), thymidine phosphorylase (nucleoside metabolism), adenosine deaminase (purine metabolism), lipoprotein lipase (metabolism of triglycerides), phenylalanine hydroxylase (metabolism of phenylalanine), guanidinoacetate methyltransferase (creatine synthesis), superoxide dismutase (antioxidant), tissue plasminogen activator (thrombolytic), streptokinase (thrombolytic), and others. The advantage of displaying therapeutic enzymes on the static capture probe is that they can remain in circulation where they may remain immobilized on the static capture thread probe 900 for long periods, as compared to majority of enzymes which when injected intravenously rapidly clear from circulation. In some embodiments, a static endovascular capture probe is used to treat THAN and other acute hyperammonemic conditions, neonatal and pediatric pathological conditions such as neonatal hyperbilirubinemia chronic bilirubin encephalopathy, or the like.

Despite many pharmacological advances, appropriate therapeutics are still lacking for numerous existing acute and chronic IgG-driven pathological conditions such as autoimmune diseases, antibody-mediated transplant rejection, and viral vector gene therapy-induced immune responses. Currently, therapeutic apheresis is used for treatment of various IgG-driven pathologies. Many IgG-driven pathological conditions such as Guillain-Barre syndrome, myasthenia gravis, paraproteinemic polyneuropathies, rapidly progressive glomerulonephritis, and antibody-mediated renal and liver transplant rejections are considered by the American Society of Apheresis (AFSA) as Category I disorders where apheresis is the first-line of therapy. However, extracorporeal blood filtration procedure requires separation of plasma from cellular components followed by removal of IgG. This approach has numerous drawbacks such as adverse side effects, long treatment duration, high cost, requirement for large complex machinery that are difficult to use, unavailable in all communities, and foremost are not patient-friendly. IdeS (immunoglobulin G-degrading enzyme of *Streptococcus pyogenes*) has emerged as a novel IgG-cleaving enzyme for treatment of many acute and chronic IgG-driven pathologies. However, this microbial-derived enzyme is highly immunogenic. Clinical studies have shown patients exhibiting acute serum sickness as a result of acute inflammatory response to the foreign enzyme, as well as generation of anti-IdeS enzymes, which prevents readministration of the enzyme for at least 6-12 months. In addition, the enzyme has a very rapid clearance time with a half-life of few hours. The combination of immunogenicity and short half-life creates a very narrow therapeutic window, and renders repeat dose administration ineffective.

In one embodiment, a static capture probe is coated with immunoglobulin degrading enzymes. Immunoglobulin degrading enzymes may include any microbial-derived enzyme capable of degradation of all immunoglobulin classes including IgG, IgM, IgA, IgD and IgE. In a preferred embodiment, the immunoglobulin degrading enzyme is IdeS (Immunoglobulin G-degrading enzyme of *Streptococcus pyogenes*). In another embodiment, the immunoglobulin degrading enzyme is IdeZ. The IdeS-immobilized probe would be surface-modified with immunomodulatory factors such as minimal CD47 peptides and thrombomodulin/EPCR proteins to mitigate cell-material interaction and prevent immune response to the detox-stick. Prevention of uptake by innate immune cells will consequently prevent generation of a humoral response. In addition, to the immunomodulatory surface modifications, this approach does not inject large sum of microbial-derived proteins into circulation for rapid uptake by the innate immune system. Potential acute serum responses are prevented by immobilizing the foreign protein and through immunomodulation. In addition, the capture probe is configured to be easily replaceable and can be continuously replaced without causing long-term consequences.

In some embodiments, a static endovascular probe 900 may include an anchor 908 comprising a set of adhesive patches to anchor the catheter to the body surface. The anchor 908 may include a clip portion that locks and stabilizes the catheter on the body surface. The anchor 908 may be formed of commercial off-the-shelf components, such as a Bard StatLock™ stabilization device.

In some embodiments, as shown in FIGS. 9B-1, 9B-2, 9C-1, and 9C-2, an endovascular apparatus 900B, 900C incorporates a static, non-rotating capture thread instead of a rotatable capture thread device, where a long-term and extensive capture is not required. In contrast to the rotational capture thread device which can have an indefinite supply of capture thread, the static endovascular probe 900 is used for short-term capture or detoxification of blood components and can be coated with a single layer or plurality of layers of capture moieties or enzymes for capture or metabolism of undesirable blood components, respectively. For example, static capture threads 932B, 932C can be used for acute pathological conditions, where the static capture thread can rapidly capture or metabolize harmful molecules to prevent a detrimental outcome in the body. Some examples of target acute pathological conditions include but are not limited to hemoglobinemia, hyperammonemia, hyperbilirubinemia, hemochromatosis, hyperkalemia, drug overdose, heavy metal poisoning, contrast-induced nephropathy, nephrogenic systemic fibrosis, azotemia, septicemia, and others.

In some embodiments, the rapid capture endovascular apparatus offers a wide range of sizes or other configurations depending on the application. The static probe, since non-rotating, can offers a wide spectrum of probe sizes, including very narrow capture probe sizes, which is beneficial in neonatal and pediatric patients who have small and difficult-to-access vasculature. One example is hyperammonemia which is a dangerous metabolic condition that manifests in cases of transient hyperammonemia of the newborn (THAN), inborn urea cycle enzyme deficiency disorders, inborn errors of branched amino acid metabolism, and liver failure. In particular, THAN is an extremely dangerous condition that occurs in preterm infant which requires immediate treatment. The present invention could be used as a safer treatment for pre-eclampsia by allowing rapid removal of systemic anti-angiogenic factors, inflammatory cytokines, and coagulation factors, while avoiding direct delivery of the therapeutics to the fetus, thereby potentially avoiding any adverse outcome in the fetus. Markedly elevated ammonia levels can rapidly lead to coma and death. Currently, hemodialysis is the most effective treatment for such conditions. However, a complex hemodialysis machine must be specially designed for neonatal patients. The lack of availability and rapid access to neonatal hemodialysis machines and highly trained physicians has been a major problem leading to high mortality. This problem can be addressed by a rapid capture probe in accordance with some embodiments. For example, the present invention would allow the rapid removal of toxic plasma ammonia levels through the immobilization of glutamine synthetase enzyme on a polymeric rod thus eliminating the need for hemodialysis.

In FIGS. 9A-1 and 9A-2, a static endovascular probe 900A includes a solid cylindrical shaft 904 coated with a single layer or plurality of layers of capture or enzymatic moieties for rapid blood detoxification. The plurality of layers may be created using any standard means in the art including using genetically encodable linkers for enzyme mediated polymerization of proteins or using layered chemical conjugation of proteins. In FIGS. 9B-1 and BA-2, a static endovascular probe 900B comprises a mandrel 905 extends through a hollow capture thread 932B. The static capture thread 992B can be shielded by a catheter shaft 904B or freely accessible in the vasculature. The mandrel 905 provides rigidity for the thread 932B to enable insertion into the vessel. The mandrel 905 provides rigidity for insertion of the static capture thread into the vasculature. It can consist of Pebax, polyurethane, polycarbonate, PTFE, polystyrene, PVC, HDPE, silicone, and a range of other materials described above for the thread material. The rapid endovascular capture probe could be replaceable, and used in combination with a vascular access port, for example, shown in FIGS. 10A and 10B, to exchange the saturated capture probe with new one if necessary.

Figure 20A:
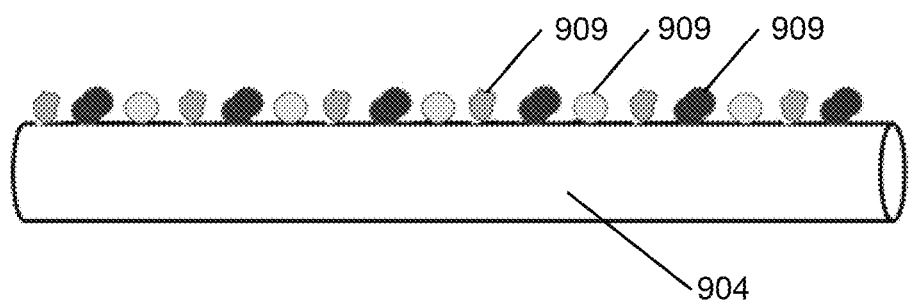
FIGS. 20A and 20B are side views of a medical oxygenation apparatus in accordance with some embodiments.
Figure 20B:
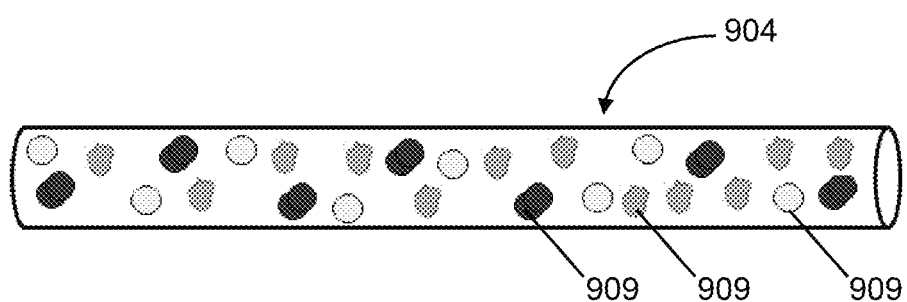

In other embodiments, the static endovascular probe may comprise a packed hollow-lumen rod (See FIG. 20B). The packing material can be any non-absorbable material. The packing material is configured to allow for high-capacity loading of capture or detoxification materials. In some embodiments, the hollow lumen rod 904 further comprises oxygenation and $CO_2$ removal material 909 including, but not limited to, hemoglobin or perfluorocarbon nanoparticles, superoxide dismutase, and carbonic anhydrase. The removal materials 909 may be embedded in a non-absorbable polymeric material through conjugation or coated on the surface of the rod (See FIGS. 20A and 20B).

Current artificial blood substitutes are hemoglobin-based oxygen carriers (HBOC) and perfluorocarbon-based oxygen carriers (PFBOC) such as oxycyte (an experimental third-generation perfluorocarbon (PFC) therapeutic oxygen carrier). These substitutes however, have issues with rapid clearance and high toxicity. In contrast, the present invention avoids potential toxicities by not releasing oxygenation/CO2 removal material into the circulation. A hollow lumen rod would enable packing of gram quantities of oxygenation material and allow superior treatment of certain diseases and traumatic lung injuries including choking, drowning, chemical inhalation, drug/alcohol abuse, respiratory failure, lung transplantation, acute respiratory distress syndrome, pulmonary hemorrhage, cardiomyopathy, myocarditis, cardiac depression, electric shock, nerve-blocking paralytic agents, and selective oxygenation of damaged tissues.

In FIGS. 9C-1 and 9C-2, a static endovascular probe 900C includes a capture thread 932C that can be stitched on the catheter shaft 904C in order to remain centered and tightly attached on the catheter. Various types of stitching techniques can be used such as back stitching, split stitch, stem stitch, and others. Holes generated at various lengths throughout the catheter shaft 904 provide the platform for the stitching.

In some embodiments, a static capture thread 932B shown in FIGS. 9B-1 and 9B-2 includes a hollow thread, for example, similar to thread 132F shown in FIG. 13F, surrounding a solid core, or encased inside a catheter shaft 904C, which inserted into the vasculature for rapid capture on undesirable molecules. As there is no rotational component, much smaller diameter threads and catheters, allowing for insertion into small vessels. In FIGS. 9D-1 and 9D-2, the core 907 can be star-shaped, hexagonal, circular, or other any configuration encased by the shaft 904D.

In some embodiments, a static thread, probe rod, or the like shown in FIGS. 9A-1 through 9D-2 can be coated with a range of moieties, for example, shown in FIG. 12, such as antibodies, proteins, peptides, chemicals, nucleic acids, porous microspheres, and affinity microspheres. For example, zirconium phosphate, fluorographene, porous organic polymers, or Ks-Amt5 protein for capture of ammonia; haptoglobin for capture of free hemoglobin; hemopexin for capture of free heme; antibodies and peptides for small and large molecules; polystyrene sulfonate for capture of potassium; deferoxamine isothiacyanate for capture of iron; chelators for metals; porous microspheres for small molecules and small proteins; porous microspheres for drug overdose, contrast agent, nitrogenous wastes, potassium, cytokines and capture of a range of small or large molecules. Sorbent polymeric porous beads consist of varying pore sizes and bead sizes that will be conjugated on the static capture thread 932 for removal of a range of molecules. The rapid endovascular capture probe 900 can be used to capture one or many different molecules at the same time.

Figure 10B:
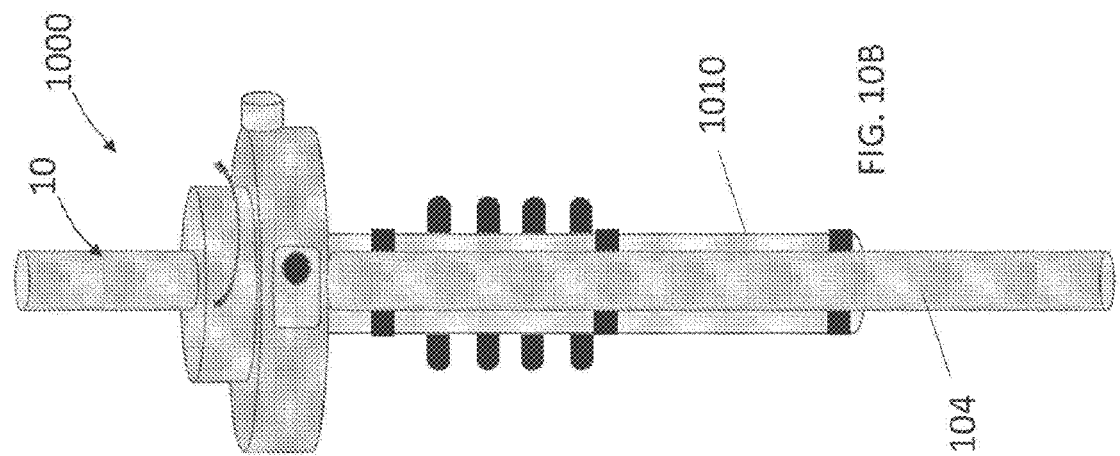
FIGS. 10A and 10B are partial cross-sectional front views of a vascular access port in an open and close position, respectively, in accordance with some embodiments.
Figure 10A:
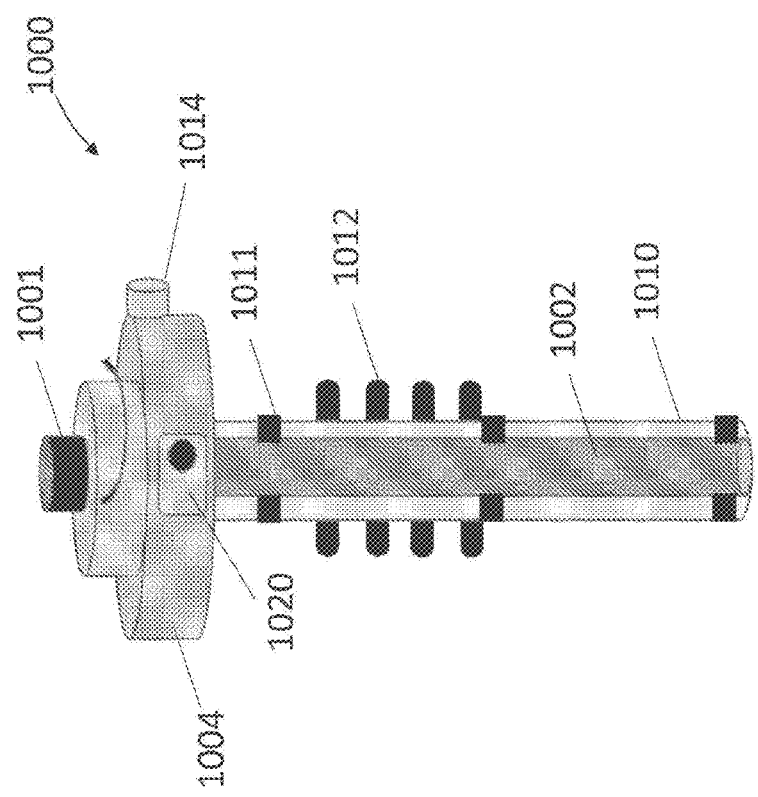

FIGS. 10A and 10B are partial cross-sectional front views of a vascular access port 1000 in an open and closed position, respectively, in accordance with some embodiments.

The vascular access port 1000 is constructed and arranged for long-term placement of the endovascular apparatus 10 shown and described in FIG. 1. For long term use, the vascular access port 1000 can be placed in the targeted treatment location so that the apparatus 10 can be repeatedly inserted and removed during one or more treatments. An access catheter 1010 can remain in place and the endovascular apparatus 10 can be attached to the vascular access port 1000 at the time of treatment. The port 1000 can remain open through the treatment (FIG. 10A) and be closed (FIG. 10B) upon the removal of the wearable enclosure 102 of the endovascular apparatus 10. This feature permits the endovascular apparatus 10 to be portable and easily used intermittently, and when used in this manner can require less invasive surgeries. The vascular access port 1000 can be constructed and arranged to be easily cleaned to prevent infections that could occur in or around the catheter insertion point.

In some embodiments, the vascular access port 1000 includes a screw cap 1001 along with a mandrel 1002 is placed inside the access port 1000 when not using the endovascular probe, or for cleaning purposes. A twist top motion of the cap 1001 allows for protrusion of the internal anchors 1011 and/or external anchors 1012. Internal anchors 1011 are intended to lock the endovascular apparatus 10 or the mandrel 1002 in place, in order to prevent leakage of any fluids from or into the body. The mandrel 1002 can be removed with the cap 1001 to provide an available hole for the catheter 10 to be inserted. External anchors 1012 are designed to securely grip the tissue at the vascular access site, to prevent dislodging of the catheter. The containment base holding the vascular access port 1000 on the skin can be used to flush disinfectants (chlorhexidine, ethanol, or other liquid or gel-based disinfectants) into the vascular access port 1000. A button 1020 or other mechanism switch allows for opening and closing of the holes at the base 1004 to disinfect the underlying skin and interior of the vascular access port 1000. A cap 1014 may be provided to allow for washing with chlorhexidine solution or other anti-microbial agents if needed.

The following are several examples of operations of an endovascular blood filtration device, in accordance with some embodiments. In describing the examples, reference is made to the wearable endovascular apparatus 10 of FIGS. 1-12.

In a first example, the collection vessel 124, also referred to as a take-up spool, is motorized, or its movements controlled by a motor of the drive system 106, pulling the thread 132 to cause it to automatically circulate through the catheter 104, which in this example has another diameter of 7 FR (2.33 mm). At the distal end of the device is a 0.79 mm diameter stainless steel pin which is fixed perpendicular to the catheter lumens. This pin is constrained in the distal tip 108 which was 3D printed on a Formlabs Form 2-3D printer from Grey FLGPGR04 resin. The thread 132 comes in through one lumen 141 in the extrusion, rotates 180 degrees around the distal pin 137, and returns through the second lumen 142 in the extrusion. The distal portion 108 of the catheter allows blood to freely flow in and out through multiple holes 143 in the outer walls. The holes 143 for the initial catheter prototype can be 1 mm in diameter, with two variations in center-to-center hole spacing of 1.5 mm and 2.5 mm, for a length of 20 cm. On the proximal side, a compliant silicone component within the catheter acts as a hemostasis valve, preventing blood from exiting the catheter passed this point, but allowing the thread 132 to enter and exit in order to circulate, constantly presenting new surface area to the blood flow for analyte binding.

To address the ability to rotate the thread 132, various thread materials and geometries were pulled through a test set up which mimicked the overall crossing profile space constraints within the catheter as well as the intended bend radius of 0.79 mm. The goal of this prototyping and testing was to maximize surface area of the selected thread 132, while still being able to pull the thread 132 around the 180 degree bend. Thread materials tested included PTFE, ePTFE, nylon and polypropylene. Variations of these materials included both flat rectangular and circular cross sectional shapes ranging in diameter from 0.30 mm to 0.71 mm. Taking into account both the test results and commercial availability, it was determined by experimentation that ePTFE suture material with a diameter of 0.51 mm was a suitable material to rotate around a 0.79 mm diameter smooth stainless steel pin 137.

To address the need to create a hemostasis valve which allowed the capture thread 132 to enter and exit, various configurations of a compliant silicone cylinder with two open lumens which are slightly undersized from the thread diameter of 0.51 mm can be inserted into the catheter. Durometers of the silicone material ranging from 2 Shore A to 60 Shore A may be used. Also varied throughout the experiments were the diameter of the valve lumens, overall length of the valve and speed of thread circulation. During experimentation, various valve configurations were considered that conservatively mimic blood pressure and flow using a peristaltic pump with water as the medium to achieve pressures of 3 psi with flow rates up to 2004 m/min to check for leakage. The testing up to this point has shown that 10 Shore A durometer silicone material with lumens in the range of 0.254 mm to 0.381 mm diameter, with valve lengths in the range of 0.25 mm to 0.35 mm are able to prevent fluid leakage for a thread pull rate of up to 4 inches per minute.

The force required to pull the thread 132 and the mechanical strength of the catheter 104 are very important factors that determine the likelihood of catheter kinking. A kink assessment fixture which secured the catheter at the proximal end and allowed the distal end to hang freely in order to demonstrate a 0 degree angle of separation from the neutral axis of the catheter (measured with no thread tension) vs. the axis of catheter measured as the thread is being circulated at the intended rate. During testing, no kinking was observed with the final endovascular probe product consisting of the PEBAX catheter with the optimized hemostasis valve.

In a second example, preliminary mechanical testing was conducted on the wearable apparatus 10. Here, the distal tip guide 137 is 3D printed on a Formlabs Form 2 3D printer using Grey FLGPGR04 resin with a 0.79 mm diameter stainless steel pin 137 bonded within it, perpendicular to the catheter shaft 104. The capture thread 132 is 0.020" diameter ePTFE. The catheter shaft 104 consists of 63 Shore D durometer clear PEBAX with two lumens. The catheter shaft ports 143 in this configuration were skived on either side of the catheter shaft 104, with spacing of 1 inch between neighboring holes 143 and approximately 3-5 mm in open hole length with 1-3 mm open hole width. On the proximal side, a compliant 10 Shore A durometer silicone component within the catheter acts as a check valve. The lumens within the check valve which the capture thread pass through are each 0.015" in diameter. The length of the endovascular apparatus prototype, measured from the far distal end to the distal side of the check valve is 230 mm. The drive system comprises a stepper motor which utilizes a Lithium Ion battery and development board to operate rotate the collection vessel in order to pull the capture thread to at the five speeds listed in FIGS. 16-18.

Utilizing the prototype, three tests were conducted to demonstrate mechanical feasibility of the device. The first test demonstrated the ability of the device to circulate the capture thread through the system. This was conducted by marking the capture thread at known distance intervals and observing the time it took for each measured distance interval to circulate through the system. The speed was then calculated based off the measured distance and time and compared with the theoretically programmed set speed. All speeds were within 15% error, and the error is expected to be due to measurement error for both time and distance and the fact that the capture thread not being under constant tension made measurement techniques challenging.

The second test demonstrated the resistance of the catheter shaft 104 to kinking while being subject to the forces which the circulating capture thread exert on it. This test was conducted by anchoring the catheter shaft at the proximal end to a piece of graph paper while leaving the distal end free to move as the capture thread circulated and measuring the resulting deflection of the distal end. The results showed that the catheter shaft 104 did not experience any kinking at any speed, and the deflection was insignificant especially at the lowest three circulation speeds.

The third test demonstrated the prevention of leakage through the check valve 134 as the capture thread circulates in a simulated use environment. This test was conducted by inserting the catheter shaft into a peristaltic pump set up in which water was the media with a flow rate of 2004 mL/min and gage pressure of 3.1 psi. The results showed no observable leakage from the check valve 134.

Although the present inventive concepts are described herein with reference to specific embodiments, various modifications and changes can be made without departing from the scope of the present inventive concepts as set forth in the claims below. Accordingly, the specification and figures are to be regarded in an illustrative rather than a restrictive sense, and all such modifications are intended to be included within the scope of the present inventive concepts. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

What is claimed is:

1. An endovascular apparatus, comprising:
   a catheter shaft constructed and arranged for insertion into a patient;
   a capture thread positioned in at least one lumen of the catheter shaft and extending from a proximal end of the catheter shaft to a distal end of the catheter shaft for capturing components of a bodily fluid from the patient, the catheter shaft including a plurality of ports for exposing the capture thread to the bodily fluid of the patient; and
an enclosure coupled to the proximal end of the catheter shaft, the enclosure including:
a feed vessel in communication with a first end of the capture thread;
a collection vessel in communication with a second end of the capture thread; and
a drive system that controls a movement of the capture thread in the catheter shaft from the feed vessel to the collection vessel.

2. The endovascular apparatus of claim 1, further comprising a strap coupled to the enclosure for removably and wearably coupling the enclosure to a chest or arm of the patient.

3. The endovascular apparatus of claim 1, wherein the endovascular apparatus is constructed and arranged as a blood processing device, wherein the capture thread includes a hollow capture thread coated with an ultrafiltration material that captures components of interest from the blood.

4. The endovascular apparatus of claim 1, wherein the endovascular apparatus is constructed and arranged as a real-time monitoring device, wherein the capture thread captures metabolites and biomarkers of the components of the bodily fluid for output to an external analysis machine.

5. The endovascular apparatus of claim 1, wherein the capture thread removes carbon dioxide from the bodily fluid and is also coated with an oxygenation material that adds oxygen to the bodily fluid.

6. The endovascular apparatus of claim 1, wherein the enclosure includes at least one access port that provides access by an external device to the capture thread.

7. The endovascular apparatus of claim 1, further comprising a check valve at the catheter shaft that prevents the bodily fluid from entering the feed vessel and the collection vessel and a safety lock that limits a flow and movement of any liquid, air, or capture thread.

8. The endovascular apparatus of claim 1, further comprising a distal tip guide about which the capture thread is positioned, and rotates about from the feed vessel to the collection vessel.

9. A medical oxygenation apparatus, comprising:
endovascular apparatus, comprising:
a catheter shaft constructed and arranged for insertion into a venous vessel of a patient; and
a thread extending from a proximal end of the catheter shaft to a distal end of the catheter shaft for oxygenation of blood from the venous vessel of the patient; and
a drive for driving the thread, the medical oxygenation apparatus further comprising:
an oxygenator, the thread extending through a chamber of the oxygenator, which oxygenates the thread and removes carbon dioxide from the thread; and
a blender that outputs a desired fraction of delivered oxygen to the oxygenator for oxygenating the thread;
an enclosure coupled to the proximal end of the catheter shaft, the enclosure including:
a feed vessel in communication with a first end of the thread;
a collection vessel in communication with a second end of the thread; and
a drive system that controls a movement of the thread in the catheter shaft from the feed vessel to the collection vessel.

10. An endovascular apparatus for capturing undesirable molecules, comprising:
a static catheter shaft constructed and arranged for insertion into a venous vessel of a patient; and
a capture element in communication with the static catheter shaft for capturing or detoxifying components of a bodily fluid from the venous vessel of the patient; and
wherein the static catheter shaft includes a hollow interior, wherein the capture element comprises a capture thread that is stitched to the hollow interior of the catheter shaft.

11. An endovascular apparatus, comprising:
a catheter shaft constructed and arranged for insertion into a venous vessel of a patient;
a capture thread positioned in at least one lumen of the catheter shaft and extending from a proximal end of the catheter shaft to a distal end of the catheter shaft for capturing components of a bodily fluid from the venous vessel of the patient as the capture thread rotates inside the catheter shaft, the catheter shaft including a plurality of ports for exposing the capture thread to the venous vessel; and
an outlet for transferring the capture thread including the captured components of the bodily fluid to an external analysis machine.

12. An endovascular apparatus, comprising:
a catheter shaft constructed and arranged for insertion into a patient;
a capture thread positioned in at least one lumen of the catheter shaft and extending through the catheter shaft from a proximal position of the catheter shaft to a distal position of the catheter shaft and returning to the proximal position of the catheter shaft, the capture thread constructed and arranged to capture components of a bodily fluid from the patient, the catheter shaft including at least one port exposing the capture thread to the bodily fluid of the patient; and
an enclosure coupled to the proximal end of the catheter shaft, the enclosure including:
a feed vessel in communication with a first end of the capture thread;
a collection vessel in communication with a second end of the capture thread; and
a drive system that controls a movement of the capture thread in the catheter shaft from the feed vessel to the collection vessel.

13. The endovascular apparatus of claim 12, wherein the drive system controls movement of the capture thread in a distal direction from the proximal position to the distal position and in a proximal direction from the distal position to the proximal position.

14. The endovascular apparatus of claim 12, further comprising a strap coupled to the enclosure for removably and wearably coupling the enclosure to a chest or arm of the patient.

15. The endovascular apparatus of claim 12, wherein the capture thread removes carbon dioxide from the bodily fluid and is also coated with an oxygenation material that adds oxygen to the bodily fluid.

16. The endovascular apparatus of claim 12, wherein the enclosure includes at least one access port that provides access by an external device to the capture thread.

17. The endovascular apparatus of claim 12, further comprising a check valve at the catheter shaft that prevents the bodily fluid from entering the feed vessel and the collection vessel; and a safety lock that limits a flow and movement of any liquid, air, or capture thread.

18. The endovascular apparatus of claim 12, further comprising a distal tip guide about which the capture thread is positioned, the distal tip guide at the distal position of the catheter shaft at which the catheter thread returns to the proximal position of the catheter shaft.

19. The endovascular apparatus of claim 12, wherein the feed vessel provides a source of capture thread and comprises a source spool for seating the source of capture thread.

20. The endovascular apparatus of claim 12, wherein the capture vessel collects returned capture thread exposed to the bodily fluid of the patient and comprises a return spool for seating the returned capture thread; and wherein the drive system controls a rotation of the return spool about an axis of the spool for pulling the capture thread through the catheter shaft.

\* \* \* \* \*